US010711265B2

(12) United States Patent
Singer et al.

(10) Patent No.: US 10,711,265 B2
(45) Date of Patent: Jul. 14, 2020

(54) ELECTROPHORESIS ASSISTED METHOD FOR PURIFYING A TARGET NUCLEIC ACID USING A DELAYED ELUTION APPROACH

(71) Applicant: Qiagen GmbH, Hilden (DE)

(72) Inventors: Thorsten Singer, Hilden (DE); Sarah Fakih, Hilden (DE)

(73) Assignee: Qiagen GmbH, Hilden (DE)

( * ) Notice: Subject to any disclaimer, the term of this patent is extended or adjusted under 35 U.S.C. 154(b) by 285 days.

(21) Appl. No.: 15/576,353

(22) PCT Filed: Jun. 1, 2016

(86) PCT No.: PCT/EP2016/062329
§ 371 (c)(1),
(2) Date: Nov. 22, 2017

(87) PCT Pub. No.: WO2016/193282
PCT Pub. Date: Dec. 8, 2016

(65) Prior Publication Data
US 2018/0148710 A1    May 31, 2018

(30) Foreign Application Priority Data
Jun. 1, 2015    (EP) .................................... 15170167

(51) Int. Cl.
*G01N 27/447*    (2006.01)
*C12N 15/10*    (2006.01)
(Continued)

(52) U.S. Cl.
CPC ......... *C12N 15/101* (2013.01); *B01D 15/203* (2013.01); *B01D 15/426* (2013.01);
(Continued)

(58) Field of Classification Search
CPC ................... G01N 27/44704; G01N 27/44739
See application file for complete search history.

(56) References Cited

U.S. PATENT DOCUMENTS

| 2002/0033338 A1* | 3/2002 | Hayashizaki .... G01N 27/44704 204/455 |
| 2009/0071830 A1 | 3/2009 | Vann et al. |
| 2011/0011742 A1* | 1/2011 | Mathers .................. C07K 1/26 204/462 |

FOREIGN PATENT DOCUMENTS

| WO | 98/10277 A1 | 3/1998 |
| WO | 00/50870 A1 | 8/2000 |
| WO | 2004/046712 A2 | 6/2004 |

OTHER PUBLICATIONS

PCT International Search Report for PCT/EP2016/062329, dated Jul. 25, 2016.

* cited by examiner

*Primary Examiner* — Alexander S Noguerola
(74) *Attorney, Agent, or Firm* — McBee Moore & Vanik IP, LLC

(57) ABSTRACT

Provided is inter alia to an electrophoresis assisted method for purifying a target nucleic acid from a nucleic acid containing sample, comprising
(a) binding the target nucleic acid to a solid phase;
(b) placing the solid phase with the bound target nucleic acid into a loading chamber of a device, wherein the device comprises a passage which comprises the loading chamber, optionally a liquid permeable separation matrix adjacent to the loading chamber, and a liquid permeable collection matrix and wherein the solid phase with the bound target nucleic acid is present in the loading chamber in a liquid medium comprising at least one water-miscible organic solvent and wherein the target nucleic acid remains bound to the solid phase in said liquid medium;
(c) generating an electric field between a cathode and an anode and using a running solution that conducts the
(Continued)

electric current, wherein the running solution dilutes the liquid medium comprised in the loading chamber resulting in elution of the bound target nucleic acid, and wherein the eluted target nucleic acid migrates according to its charge in the electric field and is retained by the collection matrix;

(d) collecting the purified target nucleic acid.

The method is particularly suitable for isolating RNA. The liquid medium delays elution of the RNA from the solid phase, thereby preventing a degradation of the RNA by e.g. RNases.

18 Claims, 5 Drawing Sheets

(51) Int. Cl.
    *B01D 15/20*     (2006.01)
    *B01D 15/42*     (2006.01)
    *B01D 57/02*     (2006.01)

(52) U.S. Cl.
    CPC ......... *B01D 57/02* (2013.01); *C12N 15/1013* (2013.01); *G01N 27/44739* (2013.01); *G01N 27/44704* (2013.01)

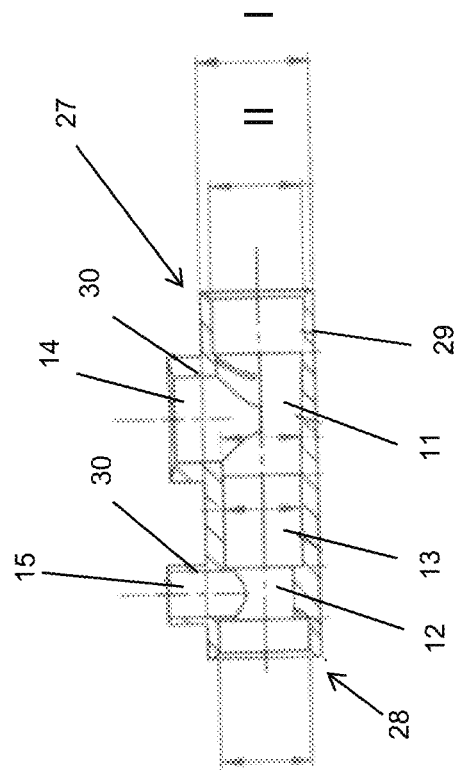
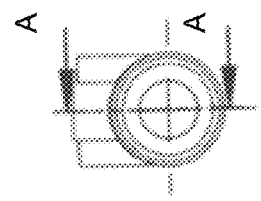
Fig. 3 ic ELECTROPHORESIS ASSISTED METHOD FOR PURIFYING A TARGET NUCLEIC ACID USING A DELAYED ELUTION APPROACH

CROSS-REFERENCE TO RELATED APPLICATIONS

This application is a National Stage entry of International Application No. PCT/EP2016/062329, filed Jun. 1, 2016, which claims priority to European Patent Application No. 15170167.9, filed Jun. 1, 2015.

BACKGROUND

Field of Invention

The invention pertains inter alia to an improved method for purifying a target nucleic acid, preferably RNA, which involves electrophoresis and to a kit that can be used for purifying a target nucleic acid by electrophoresis.

Description of Related Art

State of the art nucleic acid isolation methods are mainly based on solid phase extraction. Nucleic acids are, were necessary, released from the sample and bound under appropriate binding conditions to a solid phase. Different principles are commonly used such as binding the nucleic acids to an anion exchange surface or binding the nucleic acids in the presence of salt and/or a water-miscible organic solvent (such as an alcohol) to a solid phase, such as in particular a silica solid phase. Methods that use a chaotropic salt in order to bind nucleic acids to a silica solid phase (e.g. a membrane or magnetic silica particles) are widely used and many commercial kits are based on this principle. These known protocols require a number of hands-on interactions after the nucleic acids were bound to the solid phase. These interactions include performing one or more washing steps and eluting the nucleic acids. The individual steps require e.g. the assembly/disassembly of spin columns and collection tubes or the resuspension/collection of magnetic beads. Especially when processing a larger number of samples successively or in parallel, these known protocols are time-consuming and cumbersome. Automated protocols require complex and expensive instrumentation with a large number of moving parts making these machines prone to mechanical disturbances.

Electric field based methods (e.g. electrophoresis, electroelution, etc.) are well known and widely used in biological labs. Agarose- and polyacrylamide electrophoresis are textbook methods. However, both methods, including their modifications and specific variations, are primarily used for analytical purposes. Preparative gel electrophoresis typically requires an additional step to recover the target nucleic acid from the gel matrix which in turn requires more or less an additional nucleic acid isolation procedure. Preparative electrophoresis is applicable for low concentrations of target nucleic acids due to the separation capacity of the gel matrix. For example, overloading an agarose gel results in broadened and smeared bands, leading to the co-isolation of unwanted sample components and thus contaminated products.

Preparative systems were developed which use electrophoresis in a more or less complicated set-up for the isolation of nucleic acids (see e.g. U.S. Pat. Nos. 8,568,580, 5,217,593, 5,340,449, 6,264,814). WO 00/71999 describes a method for isolating nucleic acids which includes an electric field based separation step. The method uses a device, which comprises a cathode chamber and an anode chamber. In-between, an intermediate assembly is present through which the nucleic acids pass on their way to the anode. WO 98/10277 discloses an electric field based nucleic acid isolation method. The nucleic acids migrate from the sample chamber to the anode, thereby passing a spacer region which provides a trap having a differential effect on desired materials. WO 97/34908 teaches a nucleic acid separation method which is based on electroelution. In the described apparatus, the anode and cathode can be shielded by membranes.

The focus of such electrophoresis assisted methods is on the isolation of DNA, even though some methods are also disclosed as being suitable for isolating RNA. However, it was found that the isolation of RNA using electrophoresis assisted methods is challenging, because RNA is susceptible to degradation, in particular by RNases.

One object of the present invention is to provide an electrophoresis based method for purifying a target nucleic acid. A further object is to provide a cost-effective method that is suitable to purify a target nucleic acid, in particular RNA, which reduces the risk that the target nucleic acid is degraded during purification. Moreover, it is one object to provide a kit that is suitable to isolate a target nucleic acid, in particular RNA, using an electrophoresis assisted method.

SUMMARY OF THE INVENTION

The present invention pertains to the purification of a target nucleic acid such as RNA using an electrophoresis assisted method. The target nucleic acid is bound to a solid phase (e.g. magnetic particles) and placed while being bound to the solid phase in the loading chamber of a passage that is formed in a device that is used for performing the electrophoresis assisted method. It was surprisingly found that such method can be significantly improved, if the solid phase with the bound target nucleic acid is present in the loading chamber in a liquid medium which comprises at least one water-miscible organic solvent. The target nucleic acid remains bound to the solid phase in said liquid medium which accordingly prevents the elution of the target nucleic acid. For performing the electrophoresis assisted method, a running solution is used, which is present in surroundings of the loading chamber, e.g. in the device and/or an electrophoresis chamber into which the device can be placed for electrophoresis. When an electric field is generated between a cathode and an anode charged molecules present in the loading chamber travel according to their charge in the electric field. A basic target nucleic acid degrading enzyme such as an RNase migrates due to its charge towards the cathode. Nucleic acids travel towards the anode. However, migration of the target nucleic acid is initially prevented because the target nucleic acid remains bound to the solid phase in the liquid medium. The running solution dilutes over time the liquid medium comprised in the loading chamber resulting in elution of the bound target nucleic acid. The delayed elution of the target nucleic acid that is achieved with the liquid medium which comprises the water-miscible organic solvent as taught herein effectively prevents or reduces the contact between target nucleic acid degrading compounds and the target nucleic acid, such as e.g. a contact between RNases and RNA. As is demonstrated in the examples, this delayed elution approach can significantly improve the purification of a target nucleic acid, in particular when being confronted with a sensitive target nucleic acid such as RNA that is prone to degradation by enzymes that can be present in the device and/or can be co-transferred with the bound target nucleic acid.

According to a first aspect, the present invention provides an electrophoresis assisted method for purifying a target nucleic acid from a nucleic acid containing sample, comprising (a) binding the target nucleic acid to a solid phase;
(b) placing the solid phase with the bound target nucleic acid into a loading chamber of a device, wherein the device comprises a passage which comprises the loading chamber, optionally a liquid permeable separation matrix adjacent to the loading chamber, and a liquid permeable collection matrix and wherein the solid phase with the bound target nucleic acid is present in the loading chamber in a liquid medium comprising at least one water-miscible organic solvent and wherein the target nucleic acid remains bound to the solid phase in said liquid medium;
(c) generating an electric field between a cathode and an anode and using a running solution that conducts the electric current, wherein the running solution dilutes the liquid medium comprised in the loading chamber resulting in elution of the bound target nucleic acid, and wherein the eluted target nucleic acid migrates according to its charge in the electric field and is retained by the collection matrix;
(d) collecting the purified target nucleic acid.

According to a second aspect, a kit for use in an electrophoresis assisted method for purifying a target nucleic acid from a nucleic acid containing sample is provided, comprising
(a) a device comprising a passage which comprises a loading chamber, optionally a liquid permeable separation matrix adjacent to the loading chamber, and a liquid permeable collection matrix; and
(b) a liquid medium comprising at least one water-miscible organic solvent in a concentration in a range of 25% to 95 (v/v);
(c) optionally a running solution;
(d) optionally a solid phase for binding the target nucleic acid;
(e) optionally a lysis reagent and/or a binding reagent.

Such kit can be used in order to perform the method according to the first aspect. In a third aspect, the present invention pertains to the use of a liquid medium comprising at least one water-miscible organic solvent in an electrophoresis assisted method for purifying a target nucleic acid for temporarily maintaining binding of the target nucleic acid to a solid phase that is placed in the loading chamber of a device that is suitable for electrophoresis assisted purification of a target nucleic acid.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

BRIEF DESCRIPTION OF THE DRAWINGS

FIGS. 1-7 depict embodiments of the present disclosure

DETAILED DESCRIPTION OF A PREFERRED EMBODIMENT

Method

Figure 1:
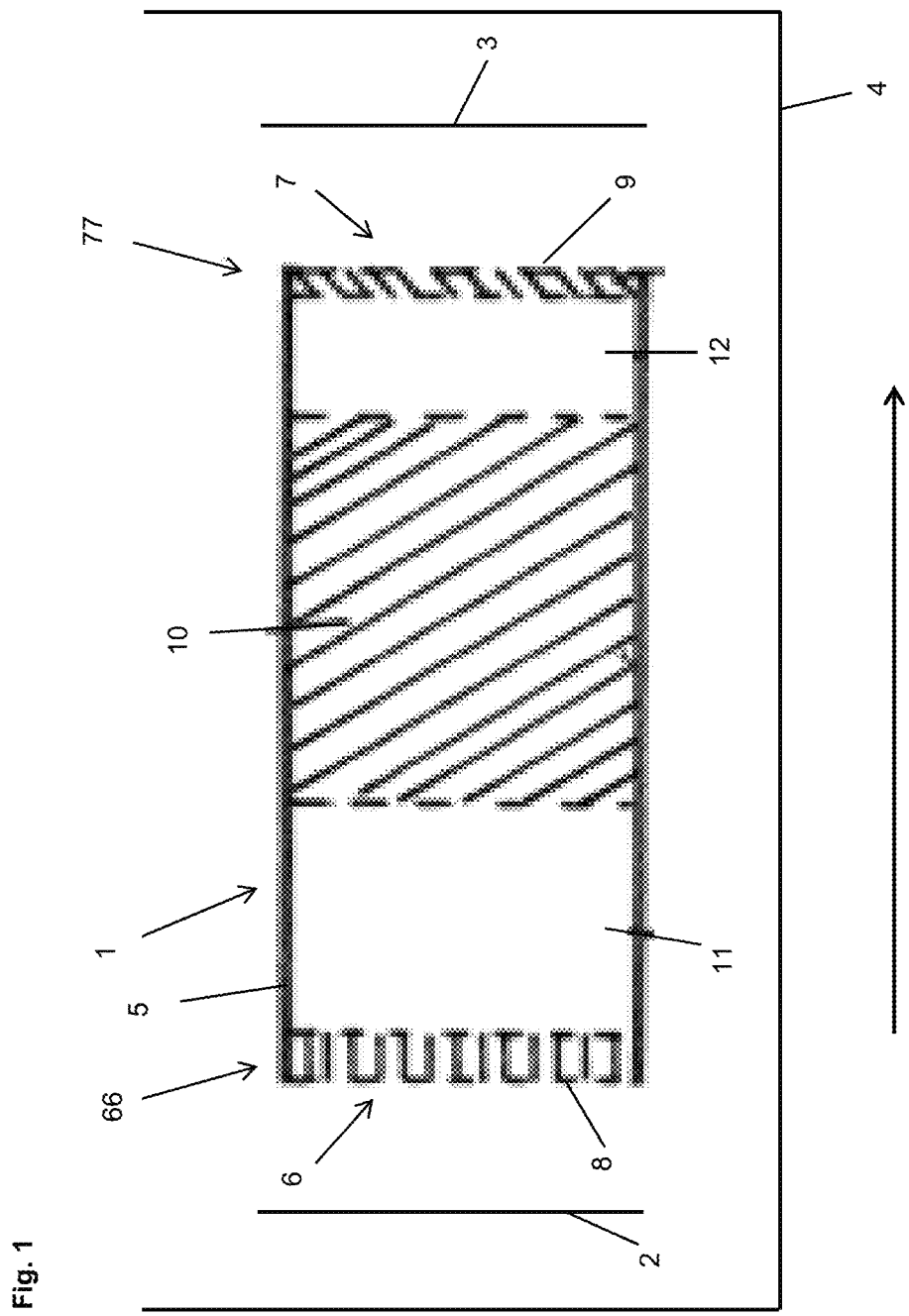

According to a first aspect, the present invention provides an electrophoresis assisted method for purifying a target nucleic acid from a nucleic acid containing sample, comprising (a) binding the target nucleic acid to a solid phase;
(b) placing the solid phase with the bound target nucleic acid into a loading chamber of a device, wherein the device comprises a passage which comprises the loading chamber, optionally a liquid permeable separation matrix adjacent to the loading chamber, and a liquid permeable collection matrix and wherein the solid phase with the bound target nucleic acid is present in the loading chamber in a liquid medium comprising at least one water-miscible organic solvent and wherein the target nucleic acid remains bound to the solid phase in said liquid medium;
(c) generating an electric field between a cathode and an anode and using a running solution that conducts the electric current, wherein the running solution dilutes the liquid medium comprised in the loading chamber resulting in elution of the bound target nucleic acid, and wherein the eluted target nucleic acid migrates according to its charge in the electric field and is retained by the collection matrix;
(d) collecting the purified target nucleic acid.

Subsequently, the invention will be explained predominantly referring to the preferred embodiment, wherein RNA is purified as target nucleic acid. This disclosure applies however mutatis mutandis to the purification of a target nucleic acid in general. Embodiments described herein by referring to a target nucleic acid in general in particular relate to and hence refer to the purification of RNA as preferred embodiment of the present invention.

It was found that it is challenging to use a method that is based on electrophoresis for purifying a target nucleic acid, in particular when being confronted with susceptible nucleic acids such as RNA. RNA is a sensitive target nucleic acid which is prone to degradation by RNases. RNA is commonly isolated from a sample by binding the RNA to a solid phase in presence of a high concentration of a salt, such as e.g. a denaturing chaotropic salt. This inhibits RNases which can be present e.g. in the sample from which the RNA is isolated. There is also a risk to introduce RNases during handling. When the solid support with the bound RNA is placed into the electrophoretic device and comes in contact with the running solution, a dilution effect occurs which can reactivate RNases that are co-transferred with the solid phase, e.g. with sample residuals. This risk in particular exists if washing steps are omitted after separating the solid phase with the bound target nucleic acid from the sample to reduce handling steps. The presence of RNases in the loading chamber can lead to destruction of RNA so that no or only degraded RNA is recovered.

The inventors found an advantageous solution for preventing that a target nucleic such as RNA is degraded during an electrophoresis assisted purification method. The isolation of a target nucleic acid such as RNA can be significantly improved with respect to yield and quality when introducing the target nucleic acid to the passage of the device while being bound to a solid phase, such as e.g. particles, preferably magnetic particles. The solid phase with the bound target nucleic acid is present in the loading chamber of the device in a liquid medium which comprises at least one water-miscible organic solvent. The solid phase with the bound target nucleic can either be contacted with said liquid medium prior to loading to the device and/or the liquid medium can be present in the loading chamber before the solid phase with the bound target nucleic acid is added. The target nucleic acid remains bound to the solid phase in said liquid medium, thereby preventing an early release of the target nucleic acid from the solid phase. This protects the target nucleic acid from coming into substantial contact with degrading compounds present in the loading chamber, e.g. RNases, in case the target nucleic acid is RNA. The liquid medium prevents the RNA from free diffusion in the loading chamber and therefore, prevents that the RNA is an easy target for RNases. The running solution dilutes the liquid medium comprised in the loading chamber over time when the electric field is applied resulting in elution of the bound target nucleic acid. E.g. after applying the electric field liquid currents can be induced in the passage of the device. This results in a liquid exchange between the loading chamber and the surrounding, which comprises the running solution. The running solution dilutes the liquid medium and generates elution conditions for the target nucleic acid. As soon as the target nucleic acid is eluted it follows the electric field lines as other charged molecules such as RNases do. RNases, which are basic proteins with a positive charge, migrate towards the cathode while RNA migrates towards the anode. Without wishing to be bound in theory, it is believed that RNAses that were co-transferred e.g. with sample residuals start to migrate essentially directly to the cathode when the electric field is applied. The bound RNA, however, can only migrate to the anode upon elution which occurs delayed due to the liquid medium which first must become diluted with running solution to create elution conditions. Therefore, there is no free diffusion of the RNA and RNases in the loading chamber when the electric field is applied which prevents the contact between RNases and RNA. The eluted target nucleic acid migrates according to its charge in the electric field through the optionally present separation matrix towards the anode and is retained by the collection matrix where it can be collected. As is demonstrated by the examples, this set-up effectively prevents a degradation of RNA and results in the isolation of high quality RNA as is demonstrated by the examples. Thereby, an improved method for the fast and simple isolation of RNA from biological samples is provided.

As is evident from the examples, the present technology allows the purification of even challenging target nucleic acids such as RNA from various sample sources. The purification is fast, simple and requires only few handling steps. The use of the liquid medium in the loading chamber to delay elution of the target nucleic acid when the electric field is applied effectively protects even sensitive target nucleic acids such as RNA from degradation as is demonstrated in the examples. The method is cost-effective as it does not require expensive compounds for protecting the target nucleic acid, such as e.g. RNase inhibitors in case of RNA as target nucleic acid. The technology of the invention can be combined with established chemistries for processing the samples such as e.g. existing and proven lysis and/or binding chemistry, e.g. involving a chaotropic salt. A major advantage compared to common isolation protocols is the possible omission of extra pipetting and handling steps like the addition of washing and elution buffers or waste removal after the target nucleic acid was bound to the solid phase. The further purification and elution of the target nucleic acid can occur within the device. Manual interactions can thereby be significantly reduced. In case of automation the workflow of the invention requires significantly less movable parts thereby significantly reducing cost of goods in production, reducing maintenance cost, and elongating maintenance intervals due to the minimized mechanical stress. The purified target nucleic acid that is retained at the collection matrix can be easily removed from the device using e.g. a pipette. In case multiple samples are processed in parallel, the processing time increases less in relation to the sample number as it does e.g. in case of common spin column based protocols because time consuming liquid and transfer steps are reduced with the present technology. When the solid phase with the bound to nucleic acids is loaded into the device and subjected to the electric field, processing time may be fixed regardless of the amount of solid phase and/or the amount of target nucleic acid bound thereto or the original size and volume of the sample which is especially useful for large volume liquid samples. This is convenient and reduces handling errors.

The organic solvent comprised in the liquid medium can be a water-miscible organic solvent, preferably selected from aprotic polar solvents and protic solvents. Also combinations of solvents may be used as water-miscible organic solvent for the purpose of the invention. The water-miscible organic solvent may have an inhibitory effect on a target nucleic acid degrading enzyme, e.g. RNase, e.g. by exhibiting protein denaturing properties. According to a preferred embodiment, the organic solvent is a protic solvent. Polar protic solvents that can be used include linear or branched C1-C5 alcohols. Water-miscible aliphatic C1-C5 alcohols such as isopropanol and ethanol are preferred and can be used as organic solvent. Also methanol is an alcohol miscible in water.

According to one embodiment, the water-miscible organic solvent is an aprotic polar solvent. Examples of such organic solvents include but are not limited to sulfoxides such as dimethylsulfoxide (DMSO), ketones such as acetone, nitriles such as acetonitrile, cyclic ethers such as tetrahydrofurane (THF) and 1,4 dioxane, lactams such as 1-methyl-2-pyrolidone (NMP) and tertiary carboxylic acid amides such as dimethyl-formamide (DMF). Such aprotic polar solvents are miscible in water. Thus, the aprotic polar solvent may be selected from sulfoxides, ketones, nitriles, cyclic or aliphatic ethers, lactames and tertiary carboxylic acid amides and preferably is selected from dimethylsulfoxide (DMSO), acetone, acetonitrile, tetrahydrofuran (THF), dioxane, respectively 1,4 dioxane, 1-methyl-2-pyrolidone (NMP) and dimethyl-formamide (DMF). Further examples include acetylacetone, diethylketone, methylethylketone, methylpropylketone, isobutylmethylketone, gamma-butyrolactone, gamma-valerolactone and propylene carbonate. The water-miscible aprotic polar solvent may be selected from the group consisting of acetone, acetonitrile, dimethyl sulfoxide (DMSO), tetrahydrofuran (THF), dioxane, and dimethylformamide (DMF), or combinations thereof. According to one embodiment, the water-miscible organic solvent is a non-alcoholic organic solvent. Examples were already mentioned above. Examples of such non-alcoholic organic solvents are aliphatic ethers, aliphatic esters, and aliphatic ketones. It is preferred that the aliphatic ethers, aliphatic esters, and aliphatic ketones comprise 2 to 10 carbon atoms. The aliphatic ether can for example be selected from the group consisting of ethylene glycol dimethyl ether, ethylene glycol diethyl ether, propylene glycol dimethyl ether, propylene glycol diethyl ether, diethylene glycol dimethyl ether, diethylene glycol diethyl ether, tetrahydrofuran and 1,4-dioxane, or a combination thereof. The aliphatic ester can for example be selected from the group consisting of propylene glycol monomethyl ether acetate and ethyl lactate, or a combination thereof. The aliphatic ketone can for example be selected from the group consisting of acetone, hydroxyacetone, and methyl ketone, or a combination thereof. The organic solvent can be a water-miscible, non-acidic organic solvent as disclosed in U.S. Pat. No. 7,329,491 B1.

The liquid medium preferably comprises the at least one water-miscible organic solvent in a concentration selected from 25% to 95% (v/v), 30% to 90% (v/v) and more preferably 35% to 85% (v/v), such as 40% to 80% (v/v). Also two or more water-miscible organic solvents can be present in the liquid medium. In this case, the indicated concentrations preferably refer to the total concentration of the contained water-miscible organic solvents.

The liquid medium is capable of conducting the electric current. It is preferably an aqueous medium. It may optionally comprise a buffering agent. E.g. buffers like MOPS, Tris, TAE, TE and TBE can be used. Generally, buffers used in electrophoresis can be used which are supplemented with a water-miscible organic solvent to provide the liquid medium. Further suitable buffers are also described herein and are known to the skilled person. A buffering agent may be comprised in a concentration of at least 0.5 mM, at least 2 mM or at least 5 mM. Ranges include 0.5 mM to 100 mM, 1 mM to 50 mM, 1.5 mM to 25 mM and 2 mM to 10 mM. A suitable concentration can be determined by the skilled person. The aqueous medium used as liquid medium may also comprise a salt, e.g. an alkali metal salt such as a halide, e.g. a chloride or an acetate, citrate, or phosphate. The salt may be comprised in a concentration from 100 mM to 1 mM, 75 mM to 5 mM, or 50 mM to 10 mM. The liquid medium may also comprise a chelating agent like EDTA or EGTA. The pH of the liquid medium may lie in a range selected from 6 to 9, 6.5 to 8.5 and 6.75 to 8. The pH also depends on the target nucleic acid and suitable pH values for processing target nucleic acids such as DNA and RNA are known to the skilled person.

According to one embodiment, the liquid medium is present in the loading chamber before the solid phase with the bound target nucleic acid is added. The loading chamber is prefilled with the liquid medium. The remaining part of the passage of the device may be pre-filled with running solution. The running solution may, however, also be introduced after the solid phase with the bound target nucleic acid was placed in the loading chamber. According to one embodiment, the solid phase with the bound target nucleic acid is contacted with the liquid medium outside the device. The liquid medium comprising the solid phase with the bound target nucleic acid is then placed into the loading chamber of the device. Thereby it is also achieved that the solid phase with the bound target nucleic acid is present in the loading chamber in the liquid medium which prevents, respectively delays elution of the target nucleic acid when the electric field is applied.

The used device comprises a passage comprising a loading chamber into which the solid phase with the bound target nucleic acid is placed. The loading chamber also receives the liquid medium which is used according to the teachings of the invention to delay elution of the target nucleic acid.

The passage of the device is closed at one end, also referred hereto as the front end, by a liquid permeable collection matrix. The collection matrix allows the passage of liquids and small ions but retains the target nucleic acid. The collection matrix thus forms a barrier for the target nucleic acid and may e.g. hold back physically the target nucleic acid. It is preferred that the collection matrix does not bind the target nucleic acid under the conditions that are used for electrophoretic purification. It shields the target nucleic acid from the anode. Details of said collection matrix are also described subsequently.

The solid phase can be held back during the purification process by a liquid permeable separation matrix which is adjacent to the loading chamber. If no separation matrix is used, the solid phase should be retained by other means. In case magnetic particles are used as solid phase, the magnetic particles may be alternatively or additionally held back in the passage of the device by the aid of a magnet in order to allow the purification of the target nucleic acids free from the solid phase. The magnetic particles can thereby be retained e.g. in the loading chamber.

However, preferably the passage comprises a liquid permeable separation matrix. The separation matrix is permeable for the running solution and the target nucleic acid. The separation matrix allows the target nucleic acid to move preferably unhindered along the electric field lines. Upon application of the electric field, the target nucleic acid begins after elution in the running solution to migrate towards the anode and passes the liquid permeable separation matrix. The use of a separation matrix is preferred because it forms a barrier in the passage and thereby achieves that macroscopic compounds such as e.g. the solid phase (e.g. magnetic beads) and/or cellular debris cannot pass the separation matrix but are retained, preferably in the loading chamber. This improves the purification result. When the purified target nucleic acid is collected from the passage (e.g. from a collection chamber), the separation matrix prevents that cellular debris or other macromolecular contaminants or a solid phase present in front of the separation matrix (e.g. in the loading chamber of the device) are being collected together with the purified target nucleic acid. The porous separation matrix can thus function as a filter. The pores of the separation matrix are sufficiently small, so that undesired solid compounds and in particular the solid phase cannot pass the separation matrix. Details of said separation matrix are also described subsequently.

According to a preferred embodiment, the other end of the passage, also referred to as rear end, is closed by a liquid permeable closing matrix. The closing matrix may form together with the separation matrix and the walls of the passage the loading chamber. The closing matrix is permeable for liquids in and outside the device. The closing matrix can shield the target nucleic acid from the cathode and may prevent that the target nucleic acid exits the device e.g. before the electric field is applied. As described herein, the passage of the device preferably comprises two end openings, wherein one end opening is closed by the collection matrix and the other end opening is closed by the closing matrix. A separation matrix is preferably present between the closing matrix and the collection matrix. The closing matrix assists to prevent that the target nucleic acid escapes the passage of the device through the rear end opening. Details of said closing matrix are described subsequently.

According to one embodiment, the device
comprises a loading chamber which is formed at least in part by the closing matrix and the separation matrix and wherein the solid phase with the bound target nucleic acid is placed into the loading chamber; and
comprises a collection chamber which is formed at least in part by the separation matrix and the collection matrix and wherein the purified target nucleic acid is collected from the collection chamber.

The collection matrix separates the collection chamber from the anode and the closing matrix separates the loading chamber from the cathode. The device is preferably a hollow, elongated tube wherein the closing matrix is located at one end region of the tube and the collection matrix is located at the other end region of the tube. Suitable embodiments are also shown in the figures.

According to one embodiment, the loading chamber comprises at least one opening in order to facilitate introduction of the solid phase with the bound target nucleic acid. The collection chamber may comprise at least one opening in order to simplify removal of the purified target nucleic acid. These openings are particularly advantageous if the device is provided as hollow body, such as in form of an elongated tube. The openings are at the top of the device and may have a "collar" to balance volume variations e.g. due to temperature or flow effects.

The passage of the device is via the collection matrix and the closing matrix, if present, in fluid communication with the exterior, such as e.g. the electrophoresis chamber. A running solution can enter and exit the passage. When the running solution enters the loading chamber of the passage, it dilutes the liquid medium so that the target nucleic acid becomes eluted from the solid phase. The running solution conducts the electric current and allows generating an electric field between a cathode and an anode that imposes a force onto molecules comprised in the passage. This force induces e.g. the migration of the target nucleic acid in the passage towards the anode. A positively charged molecule, e.g. a protein, such as an RNase, will migrate to the cathode and thereby becomes separated from the target nucleic acid. Neutral inhibitors predominantly do not move and remain in the loading chamber. Small negatively charged inhibitors can according to one embodiment pass the separation matrix and the collection matrix and exit the device and/or are flushed out of the passage at the cathodic side in case a device set-up is used, which induces a flow into the direction of the cathode.

The device can be prepared or pre-filled with the closing matrix, the separation matrix and the collection matrix. Closing matrix, separation matrix and the collection matrix can be fixed relative to each other. Closing matrix and collection matrix preferably terminate the passage with regard to the fluidic transfer into and out of the device and therefore control the liquid flow into and out of the passage.

As is described herein, the device is preferably a hollow, elongated body with openings at both ends, thereby forming a hollow passage which is likewise elongated. The device can be a replaceable unit. According to one embodiment, it is a discrete body that can be placed into an electrophoresis chamber when performing the method and does not comprise electrodes. According to a further embodiment, the device is provided as integrated cartridge which comprises the electrodes and a reservoir for the running solution. Such device can be provided as closed system e.g. for diagnostic applications. It comprises openings for entry and removal of the target nucleic acid and may comprise circuit points. Preferably, the device is a disposable consumable what is convenient for the user.

According to one embodiment, the device has an elongated body, preferably tube-shaped, which comprises in the passage the loading chamber that is formed at least in part by a liquid permeable closing matrix and a liquid permeable separation matrix and wherein the solid phase with the bound target nucleic acid is placed into the loading chamber, preferably through an opening, and wherein the device comprises in the passage a collection chamber that is formed at least in part by the separation matrix and the collection matrix and wherein the eluted target nucleic acid is collected from the collection chamber, preferably through an opening in the device.

Preferably, a device is used which does not comprise the electrodes for generating the electric field and accordingly, does not comprise a functional cathode and/or a functional anode. This is preferred, because it allows designing the device as consumable that can be used in combination with an electrophoresis chamber. After use, the device can be disposed. Hence, the device may be provided as a discrete body, preferably as cartridge, which is at least during the electrophoretic separation step placed into an electrophoresis chamber which comprises the electrodes for generating the electric field. The passage of the device is via the collection matrix and the closing matrix, if a closing matrix is present, in fluid communication with the electrophoresis chamber. The electrophoresis chamber may be filled with running solution when the device is placed or mounted in the chamber or in advance thereto. The device and the electrophoresis chamber may comprise the same running solution. According to the invention, the loading chamber comprises the liquid medium when the electric field based separation is started in order to prevent an early elution of the target nucleic acid, e.g. RNA, which would make it prone to degradation. By delaying the elution over time, the electric field can impose a force on charged molecules that are not bound to the solid phase and can induce e.g. migration of RNases to the cathode. Such degrading compounds that have a positive charge are thus directed towards the opposite direction than the target nucleic acid migrates.

The electrodes comprised in the electrophoresis chamber are preferably adapted in size and dimension to the device. This secures a maximal energy transfer (electric to kinetic) from electrode to the target nucleic acid.

In a preferred embodiment the length of the device is 1.25 cm to about 7 cm, preferred about 1.5 cm to about 6 cm, more preferred about 1.75 cm to 5 cm, and even more preferred about 2 cm to 4 cm, e.g. 2.5 cm to 3 cm. A small size simplifies the handling of the device and has advantages regarding the field strength that can be used.

The passage that is formed in the device preferably has a cross section, preferably diameter, in the mm to cm range. E.g. the cross section can lie in the range selected from 1 mm to 30 mm, 1.5 mm to 25 mm, 2 mm to 20 mm, 2.5 mm to 15 mm and 3 mm to 10 mm. The device, respectively the provided passage, is preferably tube-shaped, so that the cross section refers to the diameter. The cross section can vary over the length of the passage and can e.g. be equal or reduced along the passage from the rear end to the front end (where the collection matrix is located).

It was found that the collection matrix has a significant influence on the fluid flow in the passage during electrophoresis. Thus, besides having a mere shielding function to prevent a contact between the target nucleic acid and the electrode, it can act like a "pump" that has a significant influence on the running solution that is comprised in the passage. The collection matrix can induce a flow, which is believed to be an electroosmotic flow. This can create as a flow within the passage of the device that is directed towards the cathode and thus provides a force that opposes the direction of the force created on the target nucleic acid by the electric field. This flow inducing effect was seen with various types of collection matrixes, including ultrafiltration membranes what was highly surprising. It was found that the strength of this flow that is induced by the collection matrix can be adjusted and/or compensated and hence can be controlled according to the desired needs by various parameters described herein, such as in particular the choice of the pore size of the collection matrix and/or the collection matrix material and furthermore, the applied electric field, in particular the field strength. These parameters can be used to ensure that the device behaves in a desired way when conducting the electrophoresis assisted method and/or adjust how quickly the liquid medium is diluted with the running solution. The closing matrix and/or the separation matrix can be additionally used to adjust and control the flow-behaviour in the passage in the desired way.

By controlling the flow behaviour within the passage it can be prevented that e.g. a loading chamber or a collection chamber provided in the passage runs empty or overflows with running solution during the electric field based purification which would be detrimental to the purification process, as the electric field can break down or the target nucleic acid can get lost. The force acting on the target nucleic acid due to the electric field is larger than the force acting on the target nucleic acid due to the induced flow in the running solution that moves into the opposite direction, i.e. towards the cathode. A flow that is created in the passage, if adjusted appropriately, is advantageous as it is capable of removing impurities from the negatively charged target nucleic acid, e.g. by flushing out at least some unwanted further elements such as impurities out of the passage at the side oriented towards the cathode. Even negatively charged molecules having a lower charge density than the negatively charged target nucleic acid can be separated thereby from the target nucleic acid. The method therefore also allows separating molecules according to their charge density in the same run. Thereby, the purity can be improved. In addition to the separation of the target nucleic acid from positively charged or neutral contaminations in the electric field, molecules with a charge density smaller than the negatively charged target nucleic acid can be flushed through the rear even if they were in total negatively charged. Smaller molecules with a negative charge density identical or even larger than the target nucleic acid are removed e.g. by passing the collection membrane. This sub-aspect can be considered to be and is also described herein as the "flow-assisted" sub-aspect, where the choice of the collection matrix and optionally other parameters as described herein is made to create a flow within the passage that is sufficiently strong to have a desired effect on the unwanted elements in the passage, such as impurities.

According to a further sub-aspect, the used collection matrix is also capable of causing a flow, which is as described believed to be an electroosmotic flow, that is directed towards the cathode. However, in this sub-aspect, a substantial flow within the passage of the device that is directed to the cathode is substantially prevented by the design of the device and/or the applied electric field strength. Thus, in this sub-aspect, a flow that is induced and hence caused by the collection matrix is compensated within the passage, thereby allowing an electro-kinetic separation according to the charge of the target nucleic acid that is substantially undisturbed by flow effects that go into the opposite direction. Such flow effects within the passage of the device are according this sub-aspect preferably minimized and hence substantially eliminated as force that acts on the charged target nucleic acid and optionally other equally charged molecules. Suitable parameters to achieve such flow compensation within the passage are described herein. This aspect of the invention can be considered to be the "electro-kinetic" aspect, where the choice of the collection matrix, other device elements (such as e.g. the presence of a closing matrix) and/or the electric field strength is made to adjust that any flows within the passage are sufficiently reduced and preferably are minimized inside the passage to not disturb the electro-kinetic driven migration of the charged target nucleic acid and optionally other equally charged molecules towards the collection matrix.

Combinations of the two sub-aspects are also feasible, depending e.g. on the target nucleic acid, such as e.g. its charge, charge density and/or the composition and complexity of the target nucleic acid containing sample, and these sub-aspects may also overlap depending on the strength of the flow that is induced by the collection matrix. According to one embodiment, a flow is created in the passage that is sufficiently strong to have an desired effect on unwanted elements that are equally charged as the target nucleic acid while at the same time the electric field is sufficiently strong to effect the movement of charged target nucleic acid into the direction of the collection matrix and thus against the induced flow.

The collection matrix is hydrophilic to ensure a continuous liquid bridge for charge transportation. The material of the collection matrix can be treated and in particular can be functionalized with suitable groups to ensure hydrophilicity. E.g. hydrophobic materials can be treated with surfactants or can be functionalized with appropriate groups to ensure wettability.

The collection matrix may comprise or consist of a charged, polarizable and/or dielectric material. Preferably, it comprises or consists of a negatively charged, negatively polarizable and/or dielectric material. As described herein, the collection matrix can induce a flow in the running solution comprised in the passage of the device.

The collection matrix is preferably porous. It can be provided by a porous filter or membrane and can be an ultrafiltration membrane. Also a combination of filters and/or membranes can be used as collection matrix, which may have the same or different characteristics with respect to material, charge, polarity and/or pore size. E.g. a positively charged or a positively polarizable filter or membrane can be used in combination with a negatively charged or negatively polarizable filter or membrane. If placed in close proximity to each other, e.g. directly adjacent to each other and hence apposing, the flow characteristics are modulated by both membranes in combination so that said combination can provide the collection matrix. When the collection matrix is located at the anode, the negatively charged or negatively polarizable filter or membrane will pump liquid into the passage while the positively charged or a positively polarizable filter or membrane pumps liquid out of the passage. Thereby, the positively charged or a positively polarizable filter or membrane can be used to attenuate a strong flow, respectively electroosmotic flow, that is induced by the negatively charged or negatively polarizable filter or membrane. This allows adjusting the flow that is created in the passage by the chosen material of the collection matrix, here a combination of two filters or membranes.

The collection matrix preferably is an ultrafiltration membrane.

Porous filters and membranes are often characterized by their exclusion limit or "cut-off". The Molecular Weight Cut Off (MWCO) is usually defined in Dalton. It can be defined as the minimum molecular weight of a globular molecule that is retained to 90% by the membrane or filter. The MWCO is chosen such that it can retain the desired target nucleic acid. The MWCO is chosen such that it can retain the target nucleic acid of the desired size. E.g. a smaller MWCO are particularly suitable for RNA, in particular if it is also desired to retain small RNA such as miRNA. According to one embodiment, the collection matrix has a MWCO that lies in the range selected from 1 kDa to 500 kDa, 3 kDa to 300 kDa, 5 kDa to 200 kDa, 5 kDa to 100 kDa and 10 kDa to 50 kDa.

The collection matrix may comprise or consist of a material selected from cellulose materials, such as cellulose, regenerated cellulose (RC), cellulose esters, preferably the cellulose materials are selected from cellulose acetate materials such as cellulose acetate, cellulose diacetate and cellulose triacetate and cellulose nitrate, silicones, polyamides, such as nylon, polyamide urea, polyvinylidene fluoride (PVDF), mineral oxides, silicon containing materials, such as siliceous materials, silica, glass, silicates, zeolites (aluminosilicates), polysulfones, polyethersulfone (PES), polyamideimide, polycarbonates, ceramics, stainless steel, silver, polyacrylonitrile (PAN), polyethylene (PE), polypropylene (PP), polytetrafluoroethylene (PTFE), polyvinyl chloride (PVC) and polypiperazinamide. Preferably, the collection matrix comprises or consists of a material selected from a cellulose material (such as a cellulose material selected from cellulose acetate materials, such as cellulose acetate, cellulose diacetate and cellulose triacetate and cellulose nitrate), PES, nylon and PVDF. More preferably, the collection matrix comprises or consists of PES, regenerated cellulose, or a cellulose acetate material, such as cellulose triacetate. Hydrophobic materials such as e.g. PE and PP can be treated in order to render them hydrophilic. This can be achieved e.g. by functionalization with suitable groups. Respective hydrophobic materials that are rendered hydrophilic are also commercially available.

According to one embodiment, an ultrafiltration membrane is used as collection matrix which has a MWCO in the range of 1 kDa to 300 kDa, 1 kDa to 200 kDa, 3 kDa to 100 kDa or 5 kDa to 50 kDa. For isolating RNA an ultrafiltration membrane is preferably used, having e.g. a MWCO in the range selected from 1 kDa to 50 kDa, 3 kDa to 20 kDa, e.g. 5 kDa to 10 kDa. Preferred materials for such ultrafiltration membrane that is used as collection matrix include, but are not limited to CA, CTA, PES and RC.

According to one embodiment, the flow within the passage is adjusted and/or compensated by the choice of one or more of parameters selected from the group consisting of the collection matrix material (which includes also combinations of materials), the pore size of the collection matrix material and/or the applied electric field strength. These parameters allow adjusting and thus controlling the flow within the passage.

Additionally, the collection matrix can be used in order to determine which type of target nucleic acid e.g. with respect to its size or topoisomerism is retained at the collection matrix.

According to one embodiment, more than one collection matrix is arranged in the passage in the order of decreasing pore size towards the collection end of the device to allow recovery of different target nucleic acids according to their size and/or configuration in different compartments of the device.

The separation matrix preferably does not provide a substantial barrier to flow effects within the device. If the separation matrix provides a substantial barrier to such flows that occur within the device, this can have the effect that e.g. the collection chamber overflows or that the separation matrix is pushed through the device. In one embodiment of the present method, a different principle is applied. In this embodiment, a separation matrix is used which does not substantially disturb flows within the passage and accordingly, does not form a barrier for such flows. Instead, the collection matrix, optionally in combination with the closing matrix and/or the electric field strength, have the task to adjust and hence control such flows by controlling the entry and exit of liquid into and out of the passage of the device. In one embodiment, the collection matrix and optionally the closing matrix are therefore the elements with the highest flow resistance and therefore control the entry and exit of liquid into and out of the passage of the device. Flows within the passage of the device, such as in particular induced by an electroosmotic flow, can thus be minimized by a careful choice/adaption of the closing and collection matrices. However, the separation matrix is preferably not designed to present a flow barrier, thereby supporting to prevent undesired leakage of liquid and hence target nucleic acid out of the passage. An overflow of the eluate chamber and/or the loading chamber can be prevented and this supports that the fluid level within the passage remains substantially equal during operation. This allows e.g. an efficient separation of the target nucleic acid according to its charge and/or charge density by the applied electric field.

The separation matrix may extend within the passage of the device over a length of 0.1 mm to 25 mm, 0.5 mm to 20 mm, 1 mm to 15 mm or 1.5 mm to 10 mm. According to one embodiment, the separation matrix extends within the passage over a length of 2 mm to 20 mm, 3 mm to 15 mm or 4 mm to 10 mm. In embodiments, the separation matrix has a length of 10 mm or less, preferably 7.5 mm or less. This also depends on the used material. It is an advantage that the device can be designed small.

A suitable material for the separation matrix has to be hydrophilic to ensure a continuous liquid bridge for charge transportation. The separation matrix is preferably porous. According to a preferred embodiment, a porous filter or membrane is used as separation matrix.

The separation matrix can comprise or consist of the same material as the collection matrix. Suitable materials were described above in conjunction with the collection matrix and it is referred to the respective disclosure which also applies with respect to the separation matrix. According to one embodiment, the separation matrix is provided by a packed bed to provide a filter function. Preferably, the separation matrix comprises or consists of a material selected from cellulose materials (examples were described above), PP, PE, nylon or PVDF. More preferably it comprises or consists of cellulose acetate or PE. It can be provided by a cigarette filter material. According to one embodiment the separation matrix is provided by a hydrophilic PE filter such as a PE frit. Hydrophobic materials such as e.g. PE and PP can be treated in order to render them hydrophilic. Suitable means to achieve hydrophilic properties are known to the skilled person and respective hydrophobic base materials that are rendered hydrophilic are also commercially available.

As described, the separation matrix is preferably porous and does not present a substantial barrier to flow effects within the passage. According to one embodiment such porous, liquid permeable separation matrix is provided by choosing an appropriate porous material for providing the separation matrix. This option is preferred and suitable examples are described above. One or more pressure equalization channels can be formed within the separation matrix in order to allow pressure equalization in case flows occur within the passage of the device. Such channels are if present provided preferably in the upper third or quarter of the separation matrix. This supports to prevent that contaminants such as cellular debris contaminate the purified target nucleic acid when it is removed e.g. from the collection chamber. According to one embodiment, no pressure equalization channels are provided.

The separation matrix may also assist in the depletion of inhibitors of downstream applications of the target nucleic acid, thereby assisting the purification result. For this purpose, the separation matrix can also provide a functionalized surface to specifically bind certain substances.

Classical electrophoretic separation materials such as agarose or PAA are not well suitable materials for providing a separation matrix that can be used in conjunction with the invention as they represent a barrier to flows that occur within the passage, in particular the flow that can be induced by the collection matrix. It was found that such materials pose a risk that the sample leaks out of the device due to flow effects, such as electroosmotic flow. This particularly, if no means for pressure equalization, such as channels in the matrix, are provided. Therefore, preferably, no gel is used as material for the separation matrix. According to one embodiment, the separation matrix does not substantially induce or support a flow effect within the passage, such as in particular an electroosmotic flow. According to one embodiment, the separation matrix neither comprises a gel. According to one embodiment, no matrix of the device, i.e. neither the closing matrix, the separation matrix nor the collection matrix, is a gel or comprises a gel.

According to one embodiment, the separation matrix is a removable discrete body that can be inserted into the passage of the device. The portion of the passage that comprises the separation matrix is also referred to herein as separation section. According to one embodiment, the device comprises more than one separation matrix. Preferably, the separation matrix and the closing matrix are provided as separate elements in the device, thereby forming a loading chamber.

The closing matrix can be used in conjunction with the collection matrix to control flows within the passage. The closing matrix can thus be additionally used to adjust and/or compensate and hence control induced flows within the passage of the device in combination with the collection matrix. Thus, according to one embodiment, a flow in the running solution comprised in the passage of the device that is directed to the cathode is adjusted and/or compensated by the choice the closing matrix material and/or the pore size of the closing matrix and additionally one or more parameters selected from the group consisting of the collection matrix material, the pore size of the collection matrix material and/or the applied electric field strength.

The closing matrix can be used e.g. as resistor to reduce the flow of fluid out of the passage through the rear end opening comprising the closing matrix. The closing matrix can thus be used to reduce the flow inside the passage towards the rear end opening. This even if the collection matrix induces an electroosmotic flow. This is advantageous in case the flow within the passage is intended to be minimized what is e.g. preferred in certain embodiments described herein, such as the electro-kinetic sub-aspect of the present method.

The closing matrix can also be used to adjust the flow within the passage to a level so that impurities are flushed out of the passage at the rear end opening, while the target nucleic acid is retained inside the passage and migrates towards the collection matrix due to the applied electrical field according to its charge and/or charge density. E.g. a large pore size of the closing matrix may support the flow-assisted sub-aspect of the present method.

The closing matrix can be designed as an additional "pump" to supplement and hence assist the flow that is induced by the collection matrix and goes towards the rear end. For this an appropriate matrix is chosen to create what is believed to be an electroosmotic flow in fluid-passages inside the material of the closing matrix upon application of an electric field. This electroosmotic flow will lead to a flow of fluid through the closing matrix out of the passage in case the closing matrix is oriented towards the cathode, which will then have an effect on the flow inside the passage of the cartridge. By choosing an appropriate matrix and an appropriate electric field, what is believed to be an electroosmotic flow inside the fluid-passages inside the closing matrix can be influenced and hence the amount of fluid being "pumped" by the closing matrix. This effect can either be used to pump fluid from outside the cartridge through the opening that is closed by the closing matrix into the passage with a certain choice of closing matrix material and electric field. With a different choice of closing matrix and electric field this effect can be used to pump fluid from inside the passage through the opening comprising the closing matrix. In this embodiment, the closing matrix supports and may enhance the flow that is induced by the collection matrix.

The closing matrix is hydrophilic. The closing matrix may comprise or consist of a charged, polarizable and/or dielectric material. Preferably, it comprises or consists of a negatively charged, negatively polarizable and/or dielectric material.

The closing matrix is preferably porous. According to one embodiment, the porous closing matrix has a pore size selected from the range of 0.1 µm to 100 µm, 0.25 µm to 50 µm, 0.5 µm to 20 µm, 0.6 µm to 15 µm, 0.7 µm to 10 µm, 0.8 µm to 7.5 µm, 0.9 µm to 5 µm and 1 µm to 3 µm. Such pore sizes are particularly suitable in case the closing matrix is made of a silicon containing material which preferably is a siliceous material, such as silica or glass.

According to one embodiment, the closing matrix has a MWCO that lies in the range selected from 1 kDa to 500 kDa, 5 kDa to 300 kDa, 10 kDa to 200 kDa, 10 kDa to 100 kDa and 10 kDa to 50 kDa.

According to one embodiment, the closing matrix, which preferably is porous, is a filter or membrane, preferably a membrane. It can be an ultrafiltration membrane or a microfiltration membrane as is demonstrated by the examples. In addition, deep bed filters may be used as closing matrix.

The closing matrix can comprise or consist of the same material as the collection matrix. Suitable materials were described above and it is referred to the respective disclosure which also applies with respect to the closing matrix. A material can be rendered hydrophilic by appropriate treatments, such as e.g. functionalization. Preferably, the closing matrix comprises or consists of a material selected from cellulose materials (such as a cellulose material selected from cellulose acetate materials, such as cellulose acetate, cellulose diacetate and cellulose triacetate, and cellulose nitrate), polyethersulfone (PES), a mineral oxide and silicon containing materials, such as siliceous materials, e.g. silica and/or glass. More preferably, the closing matrix comprises or consists of regenerated cellulose (RC), a cellulose acetate material or a siliceous material such as silica and/or glass.

According to one embodiment, a siliceous fiber membrane, also referred to as fiber fleece, e.g. made of silica or glass, is used as closing matrix. It may have an average pore size that lies in a range selected from 0.5 µm to 10 µm, 0.75 µm to 5 µm and 1 µm to 3.5 µm. This embodiment is preferred. This embodiment is particularly preferred when isolating the target nucleic acid according to the electro-kinetic sub-aspect of the invention but can also be used in the flow-assisted sub-aspect.

According to one embodiment, the closing matrix has a pore size that is larger than the pore size of the collection matrix. The closing matrix is here preferably made of a cellulose acetate material, e.g. cellulose acetate or a siliceous material. Suitable embodiments and pore sizes were described above. According to one embodiment, the closing matrix is made of a siliceous material, preferably silica or glass, and has a pore size that lies in the range of 0.5 µm to 10 µm, 0.75 µm to 7.5 µm, 0.75 µm to 5 µm and preferably 1 µm to 3.5 µm. Having a closing matrix with a larger pore size can support the pressure equalization in the passage (e.g. in the loading chamber) which assists in that an overflow of running solution out of the passage is prevented.

According to a further embodiment, the closing matrix has a pore size that lies in the same range as the pore size of the collection matrix and wherein the closing matrix and the collection matrix have a MWCO in a range between 1 kDa and 300 kDa, preferably 3 kDa and 200 kDa, more preferred 5 kDa to 150 kDa such as 10 kDa to 100 kDa. This combination of closing matrix and collection matrix helps to suppress flows within the passage thereby allowing a substantially unhindered purification along the electric field lines.

In a preferred embodiment, wherein the device is placed in an electrophoresis chamber with the closing matrix facing the cathode, the closing matrix preferably allows positively charged inhibitors that are small enough to pass through the closing matrix to exit the device through the closing matrix when the electric field is applied. Moreover, in case a flow-assisted purification is performed, also negatively charged inhibitors/impurities can exit the passage through the closing matrix, if their charge density is sufficiently small to prevent migration of these negatively charged inhibitors/impurities against the induced flow towards the anode in the applied electrical field.

According to one embodiment, the separation matrix is made of the same material as the closing matrix. This embodiment is e.g. feasible for use in the flow-assisted sub-aspect of the invention. According to one embodiment, the separation matrix and the closing matrix comprises or consists of a material selected from cellulose materials (examples were described above), PP, PE, nylon or PVDF. They may comprise or consist of cellulose acetate or PE. According to one embodiment the separation matrix and the closing matrix is provided by a hydrophilic filter made of cellulose acetate or PE, such as e.g. a PE frit which is rendered hydrophilic. The closing matrix and the separation matrix can be provided e.g. by a cigarette filter material (cellulose acetate) as is demonstrated by the examples.

As described above, a further desired flow of running solution relates to the "electrokinetic" sub-aspect, where the choice of the collection matrix, preferably in combination with a closing matrix, and electric field strength is made to create a flow sufficiently reduced within the passage to not disturb the electric-field driven transport of the charged target nucleic acid and optionally other equally charged molecules towards the collection matrix. To optimize the flow characteristics within the device, the closing matrix and the collection matrix can be adapted such that the flow of the running solution through the device is substantially static. The separation matrix, the collection matrix and the closing matrix can be adapted to each other as described herein to allow pressure equalization e.g. in case an electroosmotic flow occurs. The collection matrix and the closing matrix are in embodiments those elements with the highest flow resistance and therefore control the entry and exit of liquid into and out of the passage. In order to suppress inner-tube flow effects, a matrix having a small pore size is used in one embodiment as closing matrix and as collection matrix. E.g. an ultrafiltration membrane can be used as closing matrix and as collection matrix. The ultrafiltration membrane may have a MWCO in the range of 1 kDa to 300 kDa, 1 kDa to 200 kDa, 3 kDa to 100 kDa or 5 kDa to 50 kDa, such as 10 kDa. For isolating RNA an ultrafiltration membrane is preferably used as collection matrix having e.g. a MWCO in the range selected from 1 kDa to 50 kDa, 3 kDa to 20 kDa, e.g. 5 kDa to 10 kDa. Preferred materials for the ultrafiltration membrane include, but are not limited to CA, CTA, RC and PES. Such ultrafiltration membranes are preferably used in combination with a separation matrix which has macropores in the micrometer range and therefore allows a substantially unhindered flow within the passage. Using an ultrafiltration membrane as closing matrix and as collection matrix is advantageous, because it allows to reduce and hence suppress flows within the passage, thereby allowing an efficient electro-kinetic separation based on charge as is demonstrated by the examples.

According to a further embodiment, an ultrafiltration membrane is used as collection matrix which has a MWCO in the range of 1 kDa to 300 kDa, 1 kDa to 200 kDa, 3 kDa to 100 kDa or 5 kDa to 50 kDa. For RNA the MWCO preferably lies in the range selected from 1 kDa to 50 kDa, 3 kDa to 20 kDa, e.g. 5 kDa to 10 kDa. Preferred materials for the ultrafiltration membrane that is used as collection matrix include, but are not limited to CA, CTA, RC and PES. The closing matrix that is used in combination is made of a porous siliceous material and can e.g. be provided by a silica or glass, e.g. in form of a fleece or membrane. Suitable embodiments were described above. The pore size of the closing matrix can be larger than the pore size of the collection matrix as was described above.

Details and design options for the device and in particular suitable and preferred combinations of matrices that can be used in the present method are also described in European applications EP 15 170 148.9 and EP 15 170 159.6 title: "Electrophoresis assisted method and device for purifying a charged target molecule from a sample" which were filed on the same day as the present application and the content of which is herein incorporated by reference.

The device preferably lacks as described electrodes and is placed for purification between the two electrodes of an electrophoresis chamber. It is advantageous that the device is small to keep the distance between the electrodes narrow. A maximal electrical current flow is desired. When the device is placed into the electrophoresis chamber, the anode is located in close proximity to the collection matrix and the cathode is located in close proximity to the closing matrix of the device if a negatively charged molecule is purified. The arrangement is reverse, if the target nucleic acid is positively charged. According to one embodiment, the distance between the electrodes is 10 cm or less, 8 cm or less, 7 cm or less, 5 cm or less, 4.5 cm or less when the device is placed into the electrophoresis chamber. According to one embodiment, the minimum distance between the electrodes is at least 2 cm, at least 2.5 cm or preferably at least 3 cm. A corresponding small design of the device is advantageously possible with the device according to the second aspect of the present invention. A small distance between the electrodes advantageously allows a relatively high field strength by minimal applied voltage. The field strength is calculated based on the voltage and the distance between the electrodes. The electrodes should be placed in close proximately to each other in order to allow the use of a low voltage. According to one embodiment, the method is operated using a field strength selected from 1 to 20V/cm, 3V/cm to 17V/cm and 5V/cm to 15V/cm, preferably 10V per cm. For example, if the electrodes have a distance of 4 cm and the field strength is 10V per cm, this amounts to a voltage of 40V. Such low voltage is advantageous, because this low energy input avoids an undesired heating of the system as was confirmed for the method of the invention by temperature monitoring during the run. According to one embodiment, the voltage applied is in the range of about 20V to about 150V, preferred about 25V to about 100V, more preferred 25V to 75V, even more preferred 25 V to 50V to achieve the field strength described above. For constant input voltage for a given chamber/buffer system the power is P=U*I. The unit is 1 W (Watt)=1 J (Joule)/s. 1 J is the heat required to raise the temperature of 1 g of water by 0.24 K. So 1 W is the power required to raise the temperature of 1 g of water in 1 second by 0.24 K. Assuming constant current (identical buffer and flow-tube geometry) the voltage is directly proportional to the input power. For example, a typical electrophoresis chamber operates with an electrode distance of 15 cm. To achieve desired electric field strength of for example 10V/cm a five-fold higher power is necessary to achieve the same field strength. Therefore these known systems need external cooling or large buffer reservoirs. These drawbacks can be avoided by the method of the invention. Preferably, an electrophoresis chamber is used that is adapted to the dimension of the device.

Even if the collection matrix does not bind the target nucleic acid under the used conditions, the target nucleic acid may become because of the electric field nevertheless closely attached to the collection matrix. This can render a complete collection of the target nucleic acid from the device difficult. To assist a substantially quantitative collection of the target nucleic acid, it is advantageous to briefly reverse the electric field in order to induce migration of the target nucleic acid away from the collection matrix. Thereby, the target nucleic acid detaches from the collection matrix and can be easily collected. The reversal is sufficiently brief to prevent that the target nucleic acid enters the separation matrix, if present. E.g. the reverse electric field can be applied for 1 to 60 s. This may also depend on the applied electric field strength. The target nucleic acid can e.g. be collected from the collection chamber of the device through an opening at the top of the collection chamber what is preferred in case the device is a hollow body such as an elongated tube.

During performance of the method, the passage is or becomes filled with a running solution to allow an electrophoretic purification of the target nucleic acid. This principle is well-known in the art. The running solution conducts the electric current and therefore comprises ions. The running solution has an ionic strength that is high enough in order to ensure that the electric current is conducted. However, if the salt concentration is too high, this is disadvantageous, because either the electric tension or the electrical current flow is hindered which can disturb the quality of the purification result. A low salt concentration is furthermore advantageous, because the running solution purifies the target nucleic acid as impurities are removed during the electric field based separation and the target nucleic acid is collected in the running solution. A low salt concentration is therefore advantageous as it allows to use the purified target nucleic acid in many down-stream reactions without requiring e.g. a desalting step. E.g. buffers that are used in gel electrophoresis of nucleic acids can be used to provide ions that carry a current and to maintain the pH at a relatively constant value. The running solution additionally functions as elution solution. It dilutes the liquid medium that is initially present in the loading chamber and which serves the purpose to prevent, respectively delay elution of the target nucleic acids. When the running buffer dilutes the liquid medium, the target nucleic acid such as RNA becomes eluted. Accordingly, the running solution is suitable to effect elution of the target nucleic acid from the solid phase wherein elution is optionally assisted by agitation and/or heating. In addition, it is advantageous to choose a running solution that is compatible with a subsequent nucleic acid analysis method, such as an amplification reaction. Suitable embodiments are described herein and are also known to the skilled person.

According to one embodiment, the running solution has an ionic strength of an ionic compound of 1 mM to 200 mM, 5 mM to 150 mM, 10 mM to 100 mM, preferred 15 mM to 75 mM and especially preferred 20 mM to 50 mM. According to one embodiment, this refers to the overall ionic strength.

The pH of the running solution can lie e.g. in a range of 6 to 9.5, 6.5 to 9 and 7 to 8.5. The suitable pH also depends on the target nucleic acid to be purified and can be chosen by the skilled person accordingly. Preferably, the running solution comprises a buffering agent. The buffering agent assists to maintain the pH during the electric field assisted purification in an acceptable range. E.g. when intending to purify a target nucleic acid, any biological buffer that is commonly used in nucleic acid elution solutions can be used as buffering agent in the running solution if it does not disturb the electric field based separation process. The buffering agent is preferably compatible with the intended downstream reaction, such as an amplification reaction. According to one embodiment, the buffer capacity of the buffering agent is such, that the pH is maintained during the electric field based purification process within 2 pH units, preferably within 1.5 pH units, more preferred within 1 pH unit.

The buffering agent may be e.g. selected from the group consisting of TRIS, MOPS, HEPES, MES, BIS-TRIS, glycine and carboxylic acids like acetate or citrate. Other biological buffers are also known to the skilled person that provide a buffering capacity in the desired pH range. According to one embodiment, the running solution comprises the buffering agent in a concentration of 7.5 mM to 150 mM, 10 mM to 100 mM, 15 mM to 75 mM, 20 mM to 70 mM, 20 mM to 65 mM, 25 mM to 60 mM and 30 mM to 55 mM.

According to one embodiment, the running solution comprises a salt, preferably an alkali metal salt, preferably in a concentration of 100 mM or less or 75 mM or less. According to one embodiment, the overall salt concentration in the running solution, including any buffering agent if present as a salt, is selected from 7.5 mM to 200 mM, 10 mM to 175 mM, 15 mM to 150 mM, 20 mM to 125 mM, 25 mM to 100 mM and 30 mM to 75 mM.

The inventors found that some classical electrophoretic solutions such as TBE buffer are less suitable as running solution because they may disturb because of their ingredients certain downstream reactions. As the target nucleic acid is collected in the running solution it should not contain components) that could disturb the intended downstream application, such as for example an amplification reaction or an enzymatic digestion. Therefore, using a running buffer as it is described herein is advantageous for the purification result and the performance of the method.

According to a preferred embodiment, the running solution comprises as buffering agent Tris in a concentration of 7 mM to 100 mM, preferably 10 mM to 75 mM and has a pH in the range selected from 6.5 to 9, 7 to 8.75 and 7.5 to 8.5, preferably pH 8. The running solution may comprise Tris in a concentration of 30 mM to 60 mM, preferably 30 mM to 50 mM and may have a pH in the range of 7.5 to 8.5, preferably pH 8. Such running buffer functions well in the method of the invention, in particular if DNA is isolated as target nucleic acid. Preferably, it does not contain a further salt in a concentration above 50 mM, above 30 mM, above 25 mM, above 20 mM, above 15 mM or above 10 mM.

According to one embodiment, the running solution does not contain a salt in addition to Tris.

According to one embodiment, the buffering agent is MOPS. According to one embodiment, a running buffer comprising MOPS in a concentration of 5 mM to 50 mM, preferably 10 mM to 25 mM and having a pH in the range of 6.5 to 7.5 is used, wherein said running buffer optionally but preferably comprises a salt, preferably an alkali metal salt such as NaCl, in a concentration selected from 5 mM to 100 mM, 10 mM to 75 mM and 15 mM to 60 mM. This embodiment is particularly suitable for isolating RNA as target nucleic acid. Also other running buffers used in RNA electrophoresis can be used.

The term "sample" is used herein in a broad sense and includes a variety of sources that contain nucleic acids. Preferably, the sample is a biological sample derived from a human, animal, plant, microorganism, virus or fungi. It can be a cell-containing sample. The sample may be a biological sample but the term also includes other, e.g. artificial samples which comprise nucleic acids. Exemplary samples include, but are not limited to body fluids and samples derived therefrom such as blood, serum, plasma, red blood cells, white blood cells, buffy coat, urine, cells, cell culture, tissues such as liver, spleen, kidney, lung, intestine, brain, heart, muscle, fat, pancreas; tumor cells, fetal cells, host and graft cells, swabs, sputum, saliva, semen, lymphatic fluid, liquor, amniotic fluid, cerebrospinal fluid, peritoneal effusions, pleural effusions, fluid from cysts, synovial fluid humor, bursa fluid, pulmonary lavage, lung aspirates, bone marrow aspirates, as well as lysates, extracts, or materials obtained therefrom. Materials obtained from clinical or forensic settings that contain or are suspected to contain nucleic acids are also within the intended meaning of the term sample. Furthermore, the skilled artisan will appreciate that lysates, extracts, or materials or portions thereof obtained from any of the above exemplary samples are also within the scope of the term sample.

The term "nucleic acid" or "nucleic acids" as used herein, in particular refers to a polymer comprising ribonucleosides and/or deoxyribonucleosides that are covalently bonded, typically by phosphodiester linkages between subunits, but in some cases by phosphorothioates, methylphosphonates, and the like. The method is suitable to purify DNA as well as RNA. DNA includes, but is not limited to all types of DNA, e.g. gDNA, circular DNA, plasmid DNA and circulating DNA. RNA includes but is not limited to hnRNA, mRNA extracellular RNA, noncoding RNA (ncRNA), including but not limited to rRNA, tRNA, IncRNA (long non coding RNA), lincRNA (long intergenic non coding RNA), miRNA (micro RNA), siRNA (small interfering RNA), snoRNA (small nucleolar RNA) and snRNA (small nuclear RNA). Preferably, the method is used for purifying RNA.

The sample may be disrupted in order to release the nucleic acids for binding. The term "disrupting" or "disruption" is used herein in broad sense and in particular encompasses the lysis of a sample. In a respective lysis step, nucleic acids are released from cells and/or can be freed from other sample components such as e.g. proteins, thereby rendering the nucleic acids accessible for isolation. Herein, it is referred to a respective disruption step also generally as lysis step, irrespective of whether nucleic acids are released from cells or whether the lysis is performed in order to release nucleic acids e.g. from proteins or other substances comprised in the sample. Different methods can be used in order to lyse a sample and suitable lysis methods are well-known in the prior art. Non-limiting examples are described in the following. The sample can be contacted for disruption, respectively lysis, with one or more lysing agents. These can be contained in a disruption reagent such as a lysis solution, e.g. a lysis buffer. RNA should be protected during lysis from degradation by nucleases. The chosen lysis conditions may also vary depending on the type of sample to be processed. Generally, the lysis procedure may include but it is not limited to mechanical, chemical, physical and/or enzymatic actions on the sample. Examples include but are not limited to grinding the sample in a bead mill or in the presence of glass beads, homogenising the sample, the application of ultrasound, heating, the addition of one or more detergents and/or the addition of protein degrading compounds, such as for example protein degrading enzymes or salts. Furthermore, reducing agents such as beta-mercaptoethanol or DTT can be added for lysis to assist denaturation of e.g. nucleases. According to one embodiment, at least one chaotropic agent, such as preferably at least one chaotropic salt, is used for lysing and hence disrupting the sample. Suitable chaotropic agents and in particular suitable chaotropic salts are known to the skilled person and are also described herein. Using a chaotropic salt for lysis has the advantage that it allows to introduce a chaotropic salt which may additionally support or already establish suitable nucleic acid binding conditions. Such methods are likewise well-known in the prior art.

For binding a target nucleic acid (e.g. DNA and/or RNA) to a solid phase, methods known in the prior art may be used. Examples of suitable isolation methods include but are not limited to silica-based purification methods, magnetic particle-based purification methods, chromatography based purification procedures, anion-exchange chromatography (using anion-exchange surfaces, such as e.g. magnetic particles) and combinations thereof. The target nucleic acid such as DNA and/or RNA is isolated from the optionally disrupted sample by binding the nucleic acid to a solid phase using appropriate binding conditions. The target nucleic acid is preferably RNA. Suitable binding conditions and solid phases for binding RNA are known to the skilled person.

The solid phase may e.g. provide a silica binding surface and/or may carry anion exchange functional groups which can bind the nucleic acid of interest. Non-limiting examples of suitable solid phases and binding conditions are also described herein. A preferred embodiment uses magnetic particles as solid phase, in particular magnetic particles with a silicon containing surface.

According to one embodiment, disruption of the sample involves the use of at least one chaotropic agent, preferably a chaotropic salt, in order to release the target biomolecule, e.g. a target nucleic acid. The chaotropic salt can be comprised in the lysis mixture, which contains the sample, in a concentration selected from the group consisting of 0.1 M to saturation, 0.5M to 5M, 0.75 M to 4.5M and 1M to 4.25M. Chaotropic salts include but are not limited to guanidinium salts such as guanidinium hydrochloride, guanidinium thiocyanate (or guanidinium isothiocyanate (GITC)) or chaotropic salts comprising thiocyanate, iodide, perchlorate, trichloroacetate or trifluroacetate and the like. Such chaotropic salts can be provided e.g. as sodium or potassium salts. Urea may also be used. One or more other additives can also be added for lysis such as detergents, chelating agents, nuclease inhibitors, in particular RNase inhibitors and the like. The disrupted sample may also optionally be further processed prior to the actual nucleic acid binding step. For example, the lysate can be homogenized; homogenization may also occur during the disruption/lysis process itself. Furthermore, the lysate can be cleared in order to remove cell debris. Lysis can also involve a proteolytic digest using a proteolytic enzyme.

According to one embodiment, step (a) comprises optionally lysing the sample and binding the target nucleic acid to the solid phase in the presence of a salt, wherein binding is optionally assisted by at least one water-miscible organic solvent. Suitable methods for lysing a biological sample and binding the RNA to a solid support are known to the skilled person and suitable methods involving e.g. the use of a chaotropic salt are also described herein. According to one embodiment, the target nucleic acid is bound in the presence of a salt, e.g. a chaotropic salt, to the solid phase which preferably is a solid phase that provides a silica surface. It is well-known that binding of the target nucleic acid to a solid phase can be enhanced by including a salt, preferably a chaotropic salt, in the binding mixture. Suitable conditions for binding nucleic acids to such a solid phase in the presence of a salt, in particular a chaotropic salt, are well-known to the skilled person. Non-limiting embodiments are also described herein.

The binding mixture may comprise one or more salts in a concentration which lies in a range of 0.1M up to the saturation limit to achieve or enhance binding of the target nucleic acid to the solid phase. The concentration may be selected from 0.1 M to saturation, 0.5M to 5M, 0.75 M to 4.5M and 1M to 4.25M. A higher concentration of a salt, in particular a chaotropic salt, can be favourable to ensure a good nucleic acid yield.

Binding of the target nucleic acid to the solid phase may be assisted by a suitable water-miscible organic solvent such as an alcohol which may be a branched or unbranched aliphatic alcohol with 1 to 5 carbon atoms and may be selected from methanol, ethanol, propanol, isopropanol and butanol and mixtures thereof. This is advantageous when isolating RNA. Preferably, isopropanol and/or ethanol is used. Alternatively, a non-alcoholic, water miscible organic solvent such as acetone, THF, DMSO or the like can be used to assist binding. Such methods are well-known in the art. Suitable concentration ranges for the water-miscible organic solvent in the binding mixture, if used, include but are not limited to ≥10%) to ≤80% (v/v), ≥15% (v/v) to ≤75% (v/v), ≥20% (v/v) to ≤70% (v/v) and ≥25% (v/v) to ≤65% (v/v). These concentration ranges are particularly preferred for an alcohol, such as ethanol or isopropanol.

Solid phases suitable for nucleic acid binding are known to the skilled person; exemplary suitable nucleic acid binding solid phases are described herein. As solid phase, a variety of materials capable of binding nucleic acids under appropriate conditions can be used. Any solid phase can be used for binding the nucleic acids. Preferably, the solid phase allows release of the bound nucleic acids under the conditions that are provided by the running solution, optionally assisted by heating, shaking and/or the electric field that is applied for electrophoresis. A silica material is particularly preferred.

Exemplary solid phases that can be used in conjunction with the present invention include, but are not limited to, compounds comprising silicon, including but not limited to, silica materials such as silica particles, silica fibres, glass fibres, silicon dioxide, diatomaceous earth, glass, alkylsilica, aluminum silicate, and borosilicate; nitrocellulose; diazotized paper; hydroxyapatite (also referred to as hydroxyl apatite); nylon; metal oxides; minerals, zirconia; alumina; polymeric supports, organic polymers, diethylaminoethyl- and triethylaminoethyl-derivatized supports, hydrophobic chromatography resins and the like. The term solid phase is not intended to imply any limitation regarding its form or design. Thus, the term solid phase encompasses appropriate materials that are porous or non-porous, permeable or impermeable, including but not limited to membranes, filters, sheets, particles, magnetic particles, beads, powders, fibers and the like. According to one embodiment, the surface of the solid phase such as e.g. a silica solid phase is not modified and is, e.g., not modified with functional groups. Particularly preferred is the use of silicon containing materials such as silica and polysilicic acid materials, borosilicates, silicates and anorganic glasses as solid phase. Here, the solid phase preferably provides a silica surface for interaction with the nucleic acid which may be bound by precipitation and/or adsorption. The term "silica surface" as used herein includes surfaces comprising or consisting of silicon dioxide and/or other silicon oxides, diatomaceous earth, silica silanes, glass, zeolithe, bentonite, alkylsilica, aluminum silicate and borosilicate. The silica surface is preferably unmodified. Therefore, the surface is not modified with nucleic acid binding ligands or other nucleic acid binding groups. According to one embodiment, the silica surface does not comprise any functional groups besides its silanol groups or other oxidized forms of silicon, like oxides. Exemplary solid phases that can be used in conjunction with the present invention include, but are not limited to, solid phases comprising a silica surface, including but not limited to, silica particles, silica fibres, glass materials such as e.g. glass powder, glass fibres, glass particles or controlled pore glass, silicon dioxide, glass or silica in particulate form such as powder, beads or frits.

According to the present invention, the use of particles, in particular magnetic particles, is preferred as such particles can be easily transferred into the device. Silica based nucleic acid isolation methods are broadly used in the prior art for isolating nucleic acids such as DNA and/or RNA and work particularly well if the binding mixture contains at least one salt, preferably a chaotropic salt and optionally an alcohol. According to one embodiment, silica particles are used that may have the form of beads. Preferably, said particles have a size of about 0.02 to 30 µm, more preferred 0.05 to 15 µm and most preferred of 0.1 to 10 µm. To ease the processing of the nucleic acid binding solid phase, preferably magnetic silica particles may be used. Magnetic particles respond to a magnetic field. The magnetic silica particles may e.g. be ferrimagnetic, ferromagnetic, paramagnetic or superparamagnetic. Suitable magnetic silica particles are for example described in WO 01/71732, WO 2004/003231 and WO 2003/004150. Further suitable silica particles are also known from the prior art and are e.g. described in WO 98/31840, WO 98/31461, EP 1 260 595, WO 96/41811 and EP 0 343 934 and also include for example magnetic silica glass particles. The use of magnetic particles is convenient, because the magnetic particles including the bound target nucleic acid can be processed easily by the aid of a magnetic field, e.g. by using a permanent magnet. This embodiment is compatible with established robotic systems capable of processing magnetic particles and also manual tools exist for processing magnetic particles. According to one embodiment, a device comprising at least one retractable magnet covered by an inert polymer that does not adsorb or retain any biological molecules or magnetic particles for transferring the nucleic acid-binding support material, e.g. a Pick-Pen® Magnet.

The above described nucleic acid binding solid phases are generally suitable for binding DNA and/or RNA depending on the used binding conditions as is known to the skilled person.

Optionally, one or more washing steps can be performed after the target nucleic acid was bound to the solid phase. Suitable washing buffers are described in the literature and well-known to those skilled in the art. However, preferably, no washing step is performed prior to placing the solid phase with the bound target nucleic acid into the passage of the device. This avoids extra handling steps.

Elution of the target nucleic acid from the solid phase in the loading chamber can be assisted as described by heating and/or agitation. The device comprising the solid phase with the bound target nucleic acid can e.g. be agitated, for example assisted by vortexing, the introduction of gas such as air into the mixture or by magnetic stirring, in order to mix the solid phase in the running solution to support elution. Such assistance (in particular by agitation) is in particular useful in case the target nucleic acid is large as is it the case e.g. with genomic DNA in order to ensure that it detaches from the solid phase when the liquid medium becomes diluted with the running solution. For smaller nucleic acids such as RNA or plasmids agitation is not required and this difference in the elution behavior can also be used in order to deplete e.g. undesired genomic contaminations in an RNA preparation when using the present method. According to a preferred embodiment, magnetic particles are used as solid phase. In this embodiment, a magnet can be used in order to support mixing of the magnetic particles within the loading chamber in order to assist the dilution and elution process. At least one magnetic stirring bar can be comprised in the loading chamber to assist the agitation of the magnetic particles that are used as solid phase (see e.g. DE 10 2007 045 474). Agitation is assisted by the use of at least one magnet, e.g. a permanent magnet or electromagnet, which is configured to interact with the magnetic material. The magnetic is preferably located external of the device, e.g. in the electrophoresis chamber.

The purified target nucleic acid can be used or analyzed e.g. to identify, detect, screen for, monitor or exclude a disease or other characteristic. The analytical methods will depend on the target nucleic acid of interest and include but are not limited to amplification technologies, polymerase chain reaction (PCR), mass spectrometry, hybridization assays, RNA or DNA sequencing, next generation sequencing, restriction analysis, reverse transcription, or any combination thereof. According to one embodiment, the purified target nucleic acid is used, optionally after reverse transcription in case of RNA, in an amplification reaction and the running solution is thus compatible with such use.

According to a preferred embodiment, the target nucleic acid is RNA. According to one embodiment, a DNase is added when isolating RNA, e.g. to the loading chamber or the collection chamber. The DNase may also be included in the liquid medium. The liquid medium should be free of RNases to prevent degradation of the RNA. According to one embodiment, the RNA is contacted with one or more RNase inhibitors in the loading chamber. The RNase inhibitor can be preloaded in the loading chamber, or the RNA can be contacted with an RNase inhibitor prior to placing it in the loading chamber. Non limiting examples include RNasin®, vanadyl complexes, antibodies and the like. The used RNase inhibitor is preferably not a salt and is compatible with the electric field based separation process. However, as is demonstrated in the examples, the use of an RNase inhibitor is not required, because the use of the liquid medium which delays elution of the bound RNA until it is over time diluted with running buffer when the electric field is applied effectively prevents degradation of the RNA. As soon as the electric field is applied and the RNA is eluted, the RNA migrates to the separation matrix and is retained at the collection matrix, e.g. in the collection chamber. RNases which might have been co-transferred together with the bound RNA into the device are retained in the loading chamber and migrate to the cathode. This reduces a contact between RNases and the RNA and improves the quality of the purified RNA.

According to one embodiment, the method is for isolating RNA as target nucleic acid from a biological sample and comprises (a) lysing the biological sample in the presence of at least one chaotropic salt and binding RNA to particles providing a silicon containing surface, wherein binding occurs in the presence of the at least one chaotropic salt and optionally at least one water-miscible organic solvent, (b) placing the solid phase with the bound RNA into a loading chamber of a device, wherein the device comprises a passage which comprises the loading chamber at one end, a liquid permeable separation matrix adjacent to the loading chamber and a liquid permeable collection matrix at the other end and wherein the solid phase with the bound RNA is present in the loading chamber in an aqueous liquid medium comprising at least one water-miscible organic solvent in a concentration that lies in the range of 30% to 90% (v/v) and wherein the RNA remains bound to the solid phase in said aqueous medium;

(c) generating an electric field between a cathode and an anode and using a running solution that conducts the electric current, wherein the running solution dilutes the aqueous liquid medium in the loading chamber resulting in elution of the bound RNA upon dilution of the aqueous liquid medium, and wherein the eluted RNA migrates according to its charge in the electric field through the separation matrix and is retained by the collection matrix while RNases migrate into the opposite direction;

(d) optionally reversing the electric field and collecting the purified RNA.

Kit

According to a second aspect, a kit for use in an electrophoresis assisted method for purifying a target nucleic acid from a nucleic acid containing sample is provided, comprising (a) a device comprising a passage which comprises a loading chamber, optionally a liquid permeable separation matrix adjacent to the loading chamber, and a liquid permeable collection matrix; and (b) a liquid medium comprising at least one water-miscible organic solvent in a concentration in a range of 25% to 95 (v/v);

(c) optionally a running solution;

(d) optionally a solid phase for binding the target nucleic acid;

(e) optionally a lysis reagent and/or a binding reagent.

Such kit can be used e.g. in the method according to the first aspect. Details of the device and the liquid medium which is used to delay elution of the target nucleic acid were described above and it is referred to the respective disclosure which also applies here. The same applies with respect to the optional kit components running solution, solid phase, lysis reagent and binding reagent.

Use

According to a third aspect, the present invention pertains to the use of a liquid medium comprising at least one water-miscible organic solvent in an electrophoresis assisted method for purifying a target nucleic acid for temporarily maintaining binding of the target nucleic acid to a solid phase that is placed in the loading chamber of a device that is suitable for electrophoresis assisted purification of a target nucleic acid. The liquid medium maintains binding of the target nucleic acid to the solid phase in the loading chamber of a device that is used for performing the electrophoresis assisted method. The liquid medium becomes diluted over time during electrophoresis with the running solution whereby the target nucleic acid becomes eluted from the solid phase. Details of the liquid medium, the device, the running solution and the overall principle were already described above and it is referred to the respective disclosure which also applies here. The target nucleic acid is preferably RNA.

Also disclosed are the following items:

1. An electrophoresis assisted method for purifying a target nucleic acid from a nucleic acid containing sample, comprising
    (a) binding the target nucleic acid to a solid phase;
    (b) placing the solid phase with the bound target nucleic acid into a loading chamber of a device, wherein the device comprises a passage which comprises the loading chamber, optionally a liquid permeable separation matrix adjacent to the loading chamber, and a liquid permeable collection matrix and wherein the solid phase with the bound target nucleic acid is present in the loading chamber in a liquid medium comprising at least one water-miscible organic solvent and wherein the target nucleic acid remains bound to the solid phase in said liquid medium;
    (c) generating an electric field between a cathode and an anode and using a running solution that conducts the electric current, wherein the running solution dilutes the liquid medium comprised in the loading chamber resulting in elution of the bound target nucleic acid, and wherein the eluted target nucleic acid migrates according to its charge in the electric field and is retained by the collection matrix;
    (d) collecting the purified target nucleic acid.

2. The method according to item 1, wherein the target nucleic acid is RNA.

3. The method according to item 1 or 2, wherein the water-miscible organic solvent has one or more of the following characteristics
    a) it is selected from aprotic polar solvents and protic solvents;
    b) it is selected from aliphatic, short chained branched or unbranched alcohols with preferably one to five carbon atoms, preferably selected from methanol, ethanol, propanol, isopropanol and butanol, more preferably selected from ethanol and isopropanol; and/or
    c) it is selected from sulfoxides, ketones, nitriles, cyclic or aliphatic ethers, lactams and tertiary carboxylic acid amides and is preferably selected from the group consisting of acetone, acetonitrile, dimethyl sulfoxide (DMSO), tetrahydrofuran (THF), dioxane and dimethylformamide (DMF).

4. The method according to one or more of items 1 to 3, wherein the liquid medium comprises the at least one water-miscible organic solvent in a concentration selected from 25% to 95% (v/v), 30% to 90% (v/v) and 35% to 85% (v/v).

5. The method according to one or more of items 1 to 4, having one or more of the following characteristics:
    a) the liquid medium is present in the loading chamber before the solid phase with the bound target nucleic acid is added; and/or
    b) the solid phase with the bound target nucleic acid is contacted with the liquid medium, and the liquid medium comprising the solid phase with the bound target nucleic acid placed into the loading chamber;
    c) the liquid medium is an aqueous medium which optionally comprises a salt and/or buffering agent;
    d) the liquid medium comprises a DNase; and/or
    e) the running solution has one or more of the following characteristics:
        i) it is suitable to effect elution of the target nucleic acid from the solid phase;
        ii) it has a pH that lies in the range of 5 to 9, preferably 6 to 8, more preferably 6.5 to 7.5;
        iii) it comprises a buffering agent which has a buffering capacity that lies within the range of pH 6 to 8, wherein preferably, the buffering agent is MOPS or Tris;
        iv) it comprises a buffering agent in a concentration selected from 7.5 mM to 100 mM, 10 mM to 75 mM, 12.5 mM to 50 mM, 15 mM to 40 mM and 17.5 mM to 30 mM;
        v) it comprises at least one salt, preferably an alkali metal salt; and/or
        vi) it is compatible with a subsequent nucleic acid analysis method.

6. The method according to one or more of items 1 to 5, wherein the solid phase has one or more of the following characteristics
    a) the solid phase is provided by particles, preferably silica or glass particles;
    b) the solid phase is provided by magnetic particles;
    c) the solid phase provides a silicon containing surface; and/or
    d) the solid phase provides a siliceous surface, preferably an unmodified siliceous surface.

7. The method according to one or more of items 1 to 6, wherein step (a) comprises optionally lysing the sample and binding the target nucleic acid to the solid phase in the presence of a salt, wherein binding is optionally assisted by at least one water-miscible organic solvent.

8. The method according to one or more of items 1 to 7, for isolating RNA as target nucleic acid from a biological sample, comprising
    (a) lysing the biological sample in the presence of at least one chaotropic salt and binding RNA to particles providing a silicon containing surface, wherein binding occurs in the presence of the at least one chaotropic salt and optionally at least one water-miscible organic solvent,
    (a) placing the solid phase with the bound RNA into a loading chamber of a device, wherein the device comprises a passage which comprises the loading chamber at one end, a liquid permeable separation matrix adjacent to the loading chamber and a liquid permeable collection matrix at the other end and wherein the solid phase with the bound RNA is present in the loading chamber in an aqueous liquid medium comprising at least one water-miscible organic solvent in a concentration that lies in the range of 30% to 90% (v/v) and wherein the RNA remains bound to the solid phase in said aqueous medium;
    (b) generating an electric field between a cathode and an anode and using a running solution that conducts the electric current, wherein the running solution dilutes the aqueous liquid medium in the loading chamber resulting in elution of the bound RNA upon dilution of the aqueous liquid medium, and wherein the eluted RNA migrates according to its charge in the electric field through the separation matrix and is retained by the collection matrix;

(c) optionally reversing the electric field and collecting the purified RNA.

9. The method according to one or more of items 1 to 8, wherein the device has an elongated body, preferably tube-shaped, which comprises in the passage the loading chamber that is formed at least in part by a liquid permeable closing matrix and the separation matrix and wherein the solid phase with the bound target nucleic acid is placed into the loading chamber, preferably through an opening; and wherein the device comprises in the passage a collection chamber that is formed at least in part by the separation matrix and a liquid permeable collection matrix and wherein the eluted target nucleic acid is collected from the collection chamber, preferably through an opening.

10. The method according to one or more of items 1 to 9, wherein the device is a discrete body, preferably a cartridge, that does not comprise electrodes for generating the electric field and wherein the device is at least during the electrophoretic separation step placed into an electrophoresis chamber which comprises the electrodes for generating the electric field and wherein the passage of the device is via a liquid permeable closing matrix and liquid permeable collection matrix in fluid communication with the electrophoresis chamber.

11. The method according to item 10, wherein the device is a hollow tube and the closing matrix is located at one end region of the tube and the collection matrix is located at the other end region of the tube and wherein the closing matrix is located in the region of the cathode and the collection matrix is located in the region of the anode and wherein preferably, the electrodes of the electrophoresis chamber are parallel to the closing matrix and the collection matrix of the device and wherein optionally, the electrodes are adapted in dimension and shape to fit the dimension and shape of the closing matrix and the collection matrix.

12. The method according to one or more of items 1 to 11, wherein
a) the collection matrix has one or more of the following characteristics
  i) it is hydrophilic;
  ii) it comprises or consists of a charged, polarizable and/or dielectric material, preferably a negatively charged, negatively polarizable and/or dielectric material;
  iii) it is capable of inducing a flow in the running solution comprised in the passage of the device;
  iii) it is porous;
  iv) it is a filter or membrane;
  v) it is an ultrafiltration membrane;
  vi) it has a MWCO that lies in the range selected from 1 kDa to 500 kDa, 3 kDa to 300 kDa, 5 kDa to 200 kDa, 7 kDa to 100 kDa and 10 kDa to 50 kDa, for RNA as target nucleic acid the MWCO preferably lies in the range selected from 1 kDa to 50 kDa, 3 kDa to 20 kDa, e.g. 5 kDa to 10 kDa;
  vii) it does not bind the target nucleic acid under the conditions that are used for electrophoretic purification; and/or
  viii) it comprises or consists of a material selected from cellulose materials, such as cellulose, regenerated cellulose (RC), cellulose esters, preferably selected from cellulose acetate materials such as cellulose acetate, cellulose diacetate and cellulose triacetate and cellulose nitrate, silicones, polyamides, such as nylon, polyamide urea, polyvinylidene fluoride (PVDF), mineral oxides, silicon containing materials, such as siliceous materials, silica, glass, silicates, zeolites (aluminosilicates), polysulfones, polyethersulfone (PES), polyamideimide, polycarbonates, ceramics, stainless steel, silver, polyacrylonitrile (PAN), polyethylene (PE), polypropylene (PP), polytetrafluoroethylene (PTFE), polyvinyl chloride (PVC) and polypiperazinamide, wherein preferably the collection matrix comprises or consists of a material selected from a cellulose material, PES, nylon and PVDF, more preferably it comprises or consists of PES, regenerated cellulose, or a cellulose acetate material;
and/or
b) the passage comprises a separation matrix which has one or more of the following characteristics
  i) it is hydrophilic;
  ii) it forms a barrier for the solid phase;
  iii) it is a filter or membrane;
  iv) it is porous and preferably has an average pore size that is smaller than the average size of the solid phase, wherein if particles are used as solid phase the average pore size of the separation matrix is smaller than the average diameter of the particles;
  v) it extends within the passage of the device over a length of 0.1 mm to 25 mm, 0.5 mm to 20 mm, 1 mm to 15 mm or 1.5 mm to 10 mm; and/or
  vi) the separation matrix comprises or consists of a material selected from cellulose materials, such as cellulose, regenerated cellulose (RC), cellulose esters, preferably selected from cellulose acetate materials such as cellulose acetate, cellulose diacetate and cellulose triacetate and cellulose nitrate, silicones, polyamides, such as nylon, polyamide urea, polyvinylidene fluoride (PVDF), mineral oxides, silicon containing materials, such as siliceous materials, silica, glass, silicates, zeolites (aluminosilicates), polysulfones, polyethersulfone (PES), polyamideimide, polycarbonates, ceramics, stainless steel, silver, polyacrylonitrile (PAN), polyethylene (PE), polypropylene (PP), polytetrafluoroethylene (PTFE), polyvinyl chloride (PVC) and polypiperazinamid, wherein preferably the separation matrix comprises or consists of a material selected from cellulose materials, PP, PE, nylon or PVDF, preferably it comprises or consists of cellulose acetate or hydrophilic PE;
and/or
c) the passage comprises a closing matrix which has one or more of the following characteristics:
  i) it is hydrophilic;
  ii) it is porous;
  iii) it is a filter or membrane;
  iv) it is an ultrafiltration membrane, a microfiltration membrane or a deep bed filter;
  v) it is porous and optionally has a pore size selected from the range of 0.1 μm to 100 μm, 0.25 μm to 50 μm, 0.5 μm to 25 μm, 0.6 μm to 15 μm and 0.7 μm to 10 μm, preferably selected from 0.8 μm to 7.5 μm, 0.9 μm to 5 μm and 1 μm to 3 μm;
  vi) it has a MWCO that lies in the range selected from 1 to 500 kDa, 5 kDa to 300 kDa, 10 kDa to 200 kDa, 10 kDa to 100 kDa and 10 kDa to 50 kDa;
  vii) it has a pore size that is larger than the pore size of the collection matrix;
  viii) it has a pore size that lies in the same range as the pore size of the collection matrix wherein said range is between 1 kDa and 300 kDa, preferably 10 kDa and 100 kDa; and/or
  ix) it comprises or consists of a material selected from cellulose materials, such as cellulose, regenerated cellulose (RC), cellulose esters, preferably selected from cellulose acetate materials such as cellulose acetate, cellulose diacetate and cellulose triacetate and cellulose nitrate, silicones, polyamides, such as nylon, polyamide urea, polyvinylidene fluoride (PVDF), mineral oxides, silicon containing materials, such as siliceous materials, silica, glass, silicates, zeolites (aluminosilicates), polysulfones, polyethersulfone (PES), polyamideimide, polycarbonates, ceramics, stainless steel, silver, polyacrylonitrile (PAN), polyethylene (PE), polypropylene (PP), polytetrafluoroethylene (PTFE), polyvinyl chloride (PVC) and polypiperazinamide, wherein preferably the closing matrix comprises or consists of a material selected from cellulose materials, polyethersulfone (PES), a mineral oxide, silicon containing materials, such as a siliceous material, more preferably it comprises or consists of regenerated cellulose (RC), a cellulose acetate material or a siliceous material.

13. A kit for use in a electrophoresis assisted method for purifying a target nucleic acid from a nucleic acid containing sample, comprising
    (a) a device comprising a passage which comprises a loading chamber, optionally a liquid permeable separation matrix adjacent to the loading chamber, and a liquid permeable collection matrix; and
    (b) a liquid medium comprising at least one water-miscible organic solvent in a concentration in a range of 25% to 95 (v/v);
    (c) optionally a running solution;
    (d) optionally a solid phase for binding the target nucleic acid;
    (e) optionally a lysis reagent and/or a binding reagent.

14. Kit according to item 13, having one or more of the following characteristics:
    a) the device has the characteristics as defined in one or more of items 9 to 12;
    b) the liquid medium has one or more of the characteristics as defined in one or more of items 3 to 5;
    c) the running solution has one or more of the characteristics as defined in item 5 e);
    d) the solid phase has one or more of the characteristics as defined in item 6; and/or
    e) the lysis reagent and/or the binding reagent comprises a salt, preferably a chaotropic salt.

15. Use of a liquid medium comprising at least one water-miscible organic solvent in an electrophoresis assisted method for purifying a target nucleic acid for temporarily maintaining binding of the target nucleic acid to a solid phase that is placed in the loading chamber of a device that is suitable for electrophoresis assisted purification of a target nucleic acid.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

As used in the subject specification and claims, the singular forms "a", "an" and "the" include plural aspects unless the context clearly dictates otherwise. Thus, for example, reference to "a separation matrix" includes a single separation matrix, as well as two or more separation matrices. Likewise, reference to "an opening, "an aperture" and the like includes single entities and combinations of two or more of such entities. Reference to "the disclosure" and "the invention" and the like includes single or multiple aspects taught herein; and so forth. Aspects taught herein are encompassed by the term "invention".

The term "solution" as used herein in particular refers to a liquid composition, preferably an aqueous composition. It may be a homogenous mixture of only one phase or a suspension of two immiscible liquids but it is also within the scope of the present invention that a solution comprises solid constituents such as e.g. precipitates or nucleic acid binding particles.

According to one embodiment, subject matter described herein as comprising certain steps in the case of methods or as comprising certain elements in the case of devices or systems, refers to subject matter consisting of the respective steps or elements. It is preferred to select and combine preferred embodiments described herein and the specific subject-matter arising from a respective combination of preferred embodiments also belongs to the present disclosure.

DESCRIPTION OF THE FIGURES

Examples of the invention and in particular the device will now be described with reference to the accompanying drawings. The described features are general design elements of the device. This also follows from the associated advantages. Therefore, even if a feature is described in conjunction with a specific embodiment of the device it is to be noted that said feature can also be used in conjunction with a different embodiment of the device, which differs with respect to other features.

FIG. 1 shows a schematic drawing of a device 1 that can be used in the method of the invention which is here shown when placed in an electrophoresis chamber. The device 1 is positioned between two electrodes 2, 3 that are located in an electrophoresis chamber 4. When an electric field is generated, electrode 2 provides the cathode and electrode 3 provides the anode in the shown set-up. The device 1 comprises a casing 5 forming a hollow body which provides a passage inside. An opening 6, 7 is formed at each end region 66, 77. The size and shape of the electrodes 2, 3 preferably correspond to the size and shape of the openings 6, 7 of the device. The passage of the device 1 comprises at the end region 66 which is oriented to electrode 2 a porous, liquid-permeable closing matrix 8 and at the end region 77 which is oriented to electrode 3 a porous, liquid-permeable collection matrix 9. Additionally, the passage of the device 1 comprises a porous, liquid permeable separation matrix 10. The closing matrix 8 forms with the casing 5 and the separation matrix 10 a loading chamber 11 which may receive the solid phase, e.g. particles, comprising bound RNA. The solid phase with the bound target nucleic acid is present in the loading chamber in a liquid medium which comprises at least one water-miscible organic solvent which maintains binding of the target nucleic acid to the solid phase. Upon dilution of the liquid medium with running buffer during electrophoresis, the target nucleic acid becomes eluted. This delayed elution effectively prevents degradation of the target nucleic acid, e.g. RNA by RNases. The separation matrix 10 forms with the casing 5 and the closing matrix 9 a collection chamber 12 which retains the purified nucleic acids. The device 1 and the electrophoresis chamber 4 are filled with a running buffer (not shown) which is in contact with the electrodes 2, 3. Upon application of an electric field, the target nucleic acid becomes upon dilution of the liquid medium eluted and migrates from the loading chamber 11 through the separation matrix 10 into the collection chamber 12 where it is retained by the collection matrix 9. The large arrow indicates the migration direction of the nucleic acids in the electric field.

Figure 2:
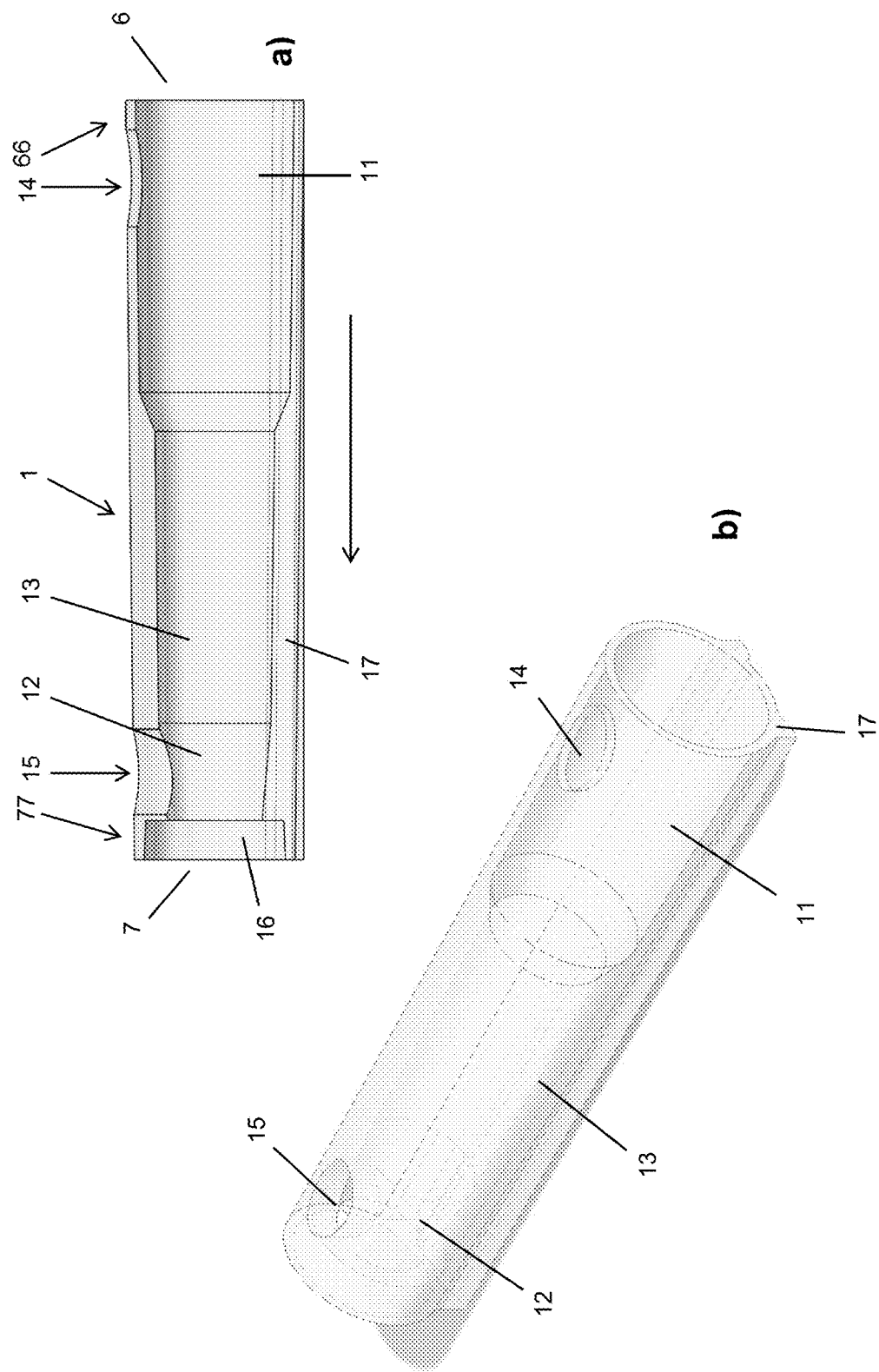

FIG. 2 shows an embodiment of a device, wherein FIG. 2a is a transparent isometric view and FIG. 2b is a longitudinal section view. In the embodiment shown in FIG. 2 the cross section of the passage is reduced from the loading section to the separation section to the elution or collection section. The device 1 has two openings 6, 7 at the two opposed end regions 66 and 77. The closing matrix, the separation matrix and the collection matrix are not shown. The device 1 has an elongated tube-shaped body what is preferred in the context of the invention. The cross section (here diameter) of the loading chamber 11 is greater than the cross section (here diameter) of the region for the separation matrix, herein referred to as the separation section 13. The cross section (here diameter) of the separation section 13 is greater than the cross section (here diameter) of the collection chamber 12 from which the eluted nucleic acids are collected. In the region of the loading chamber 11 an opening/aperture 14 is formed. The solid phase with the bound nucleic acid can be placed into the loading chamber 11 of the device 1 via said opening/aperture 14. This simplifies loading of the device from the top. In the region of the collection chamber 12 an opening/aperture 15 is formed. The purified target nucleic acid is retained by the collection matrix in the collection chamber 12 and can be removed from the collection chamber through this opening 15, e.g. using a pipette. This simplifies the collection. In the end region 77 a retainer is formed for mounting the collection matrix. In the shown embodiment, a circle-shaped block 16 is formed in the housing of the device against which the collection matrix can rest, thereby fixing the collection matrix within the device. The collection matrix can for example be hold in the position of abutment against the block 16 by a ring. The device comprises in the shown embodiment a supporting base 17 in the shape of a pedestal. This supporting base simplifies secure placement of the device in an electrophoresis chamber. The loading chamber 11 may be larger than the collection chamber 12, as it is shown in the embodiment of FIG. 2. A small collection chamber is advantageous as it concentrates the purified target nucleic acid in the collection chamber 12 because the running solution volume in which the target nucleic acid is contained is reduced.

FIG. 3 shows a preferred embodiment of a device that can be used in conjunction with the present method cut along A-A. The device is designed as elongated tube and receives a closing matrix, a separation matrix and the collection matrix (the matrices are not shown). The device may have an overall length in the range of 2.5 to 3.5 cm, in the shown embodiment 2.83 cm. The outer cross section I of the device (diameter in the shown embodiment) is the same over the complete device and hence at the rear end 27 and front end 28. At the rear end 27 a retainer is formed for mounting the closing matrix. In the shown embodiment, a circle-shaped block 29 is formed in the housing of the device which receives the closing matrix. The closing matrix confines together with the separation matrix and the device housing the loading chamber. An aperture 14 at the top of the device, above the loading chamber, is provided for loading. It has a collar 30 in order to prevent that running solution enters or exits the device during operation. Such collar 30 is also provided at aperture 15 for collecting the purified target nucleic acid. The collars can extend in a tube-like fashion. Loading aperture 14 is preferably larger than collection aperture 15. The loading chamber 11 is substantially larger than the collection chamber 12. This is achieved in the shown embodiment by making the inner cross section of the passage section which provides the loading chamber 11 substantially larger than the inner cross section of the passage section that provides the collection chamber 12. In addition, the loading chamber 11 also stretches over a longer section of the passage than the collection chamber 12. Therefore, the loading chamber 11 can receive a larger amount of liquid than the collection chamber 12. This is advantageous, as it results in a concentration effect. Adjacent to the loading chamber 11 the separation section 13 is provided which receives in use the separation matrix. The collection chamber 12 is located adjacent to the separation matrix. An aperture 15 is provided at the top of the collection chamber 12 to simplify removal of the purified target nucleic acid. At the front end 28 again a substantially circle-shaped block is formed in the housing of the device against which the collection matrix (not shown) can rest thereby fixing the collection matrix within the device. The collection matrix can be hold in the position of abutment against the block by a retainer ring. The collection matrix confines together with the separation matrix and the housing of the device the collection chamber 12. The passage that is formed between the rear end 27, respectively the comprised closing matrix and the front end 28, respectively the provided collection matrix, has in the shown embodiment a cross section II which is reduced from the loading section to the separation section to the collection section, what is one optional design element of the device. The passage can also be tapered within a certain section as it is evident from the loading chamber 11. The passage or sections thereof may generally have a decline of approximately 3% to 5%, in particular 4%. The advantages of a tapered passage are described herein. The front end 28 which receives the collection matrix which can be held e.g. by a ring has again a larger diameter than the collection chamber 12. In the shown embodiment, the cross section of the opening at the front end 28 is the same as at the block 29 at the rear end 27. Therefore, the cross section enlarges again at the front end of the passage, respectively the device. This is advantageous, as thereby the rear end 27 and the front end 28 have substantially the same size and dimension which is favourable with respect to the electrodes that are used in the electrophoresis chamber in combination with this device. It allows to use electrodes that have the same size and dimension. According to a preferred embodiment, the device is as is shown in FIG. 3 an elongated tube which preferably is except for the openings and apertures a closed tube. The inner diameter of the tube which provides the passage lies according to one embodiment in the range of 2.5 mm to 10 mm, preferably 3 mm to 9 mm, more preferably 3.5 mm to 8 mm. According to one embodiment, the separation section has a diameter within the passage that lies in a range of 4 mm to 8 mm, preferably 5 mm to 7 mm. As is shown, the diameter of the collection chamber 12 is smaller than the diameter in the separation section 13. At the front end 28, the device enlarges again and has the same diameter at the front end 28 as at the rear end 27.

Figure 4:
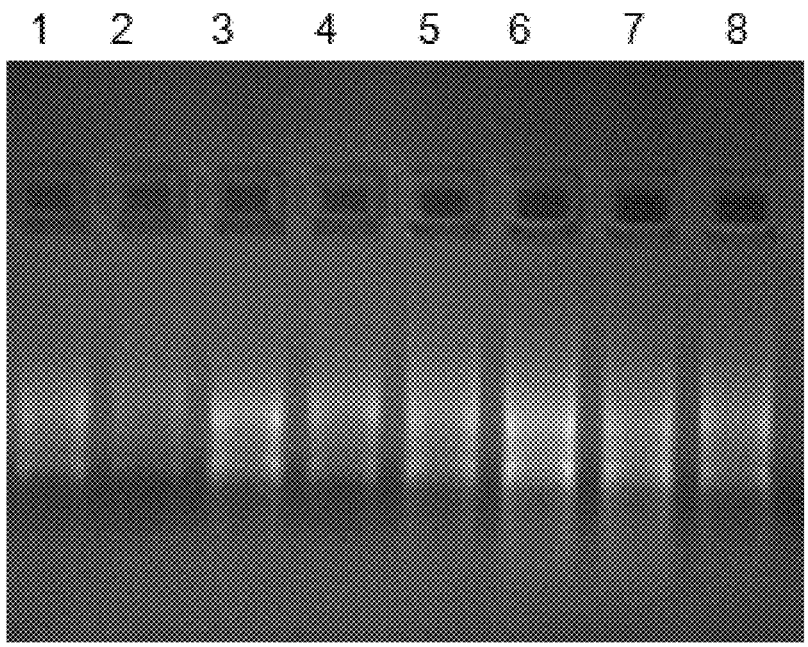

FIG. 4 shows eluates from RNA collected with an electrophoresis assisted procedure (comparative example): lanes 1-4: 100 kDa membrane; lanes 4-8: 10 kDa membrane.

Figure 5:
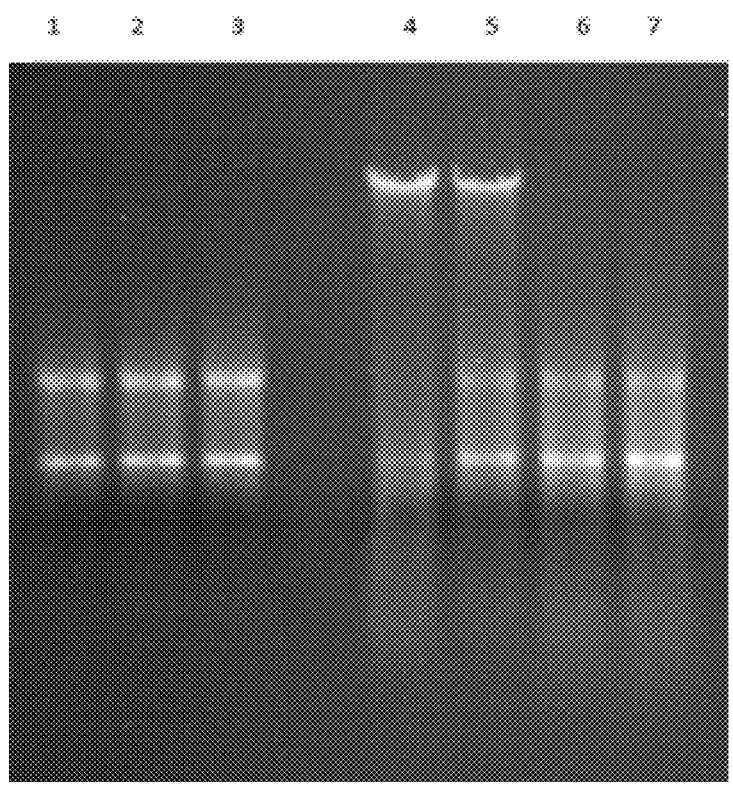

FIG. 5 shows the results of example 3 wherein RNA was purified inter alia with an electrophoresis assisted procedure using RNase inhibitors.

Figure 6:
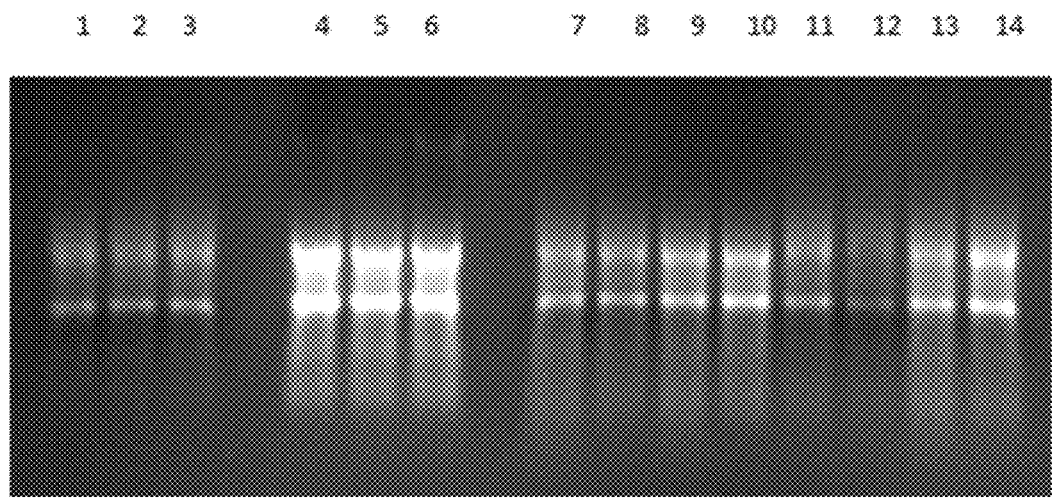

FIG. 6 shows the results of example 4 wherein RNA was purified inter alia using different electrophoresis assisted procedures with delayed elution.

Figure 7:
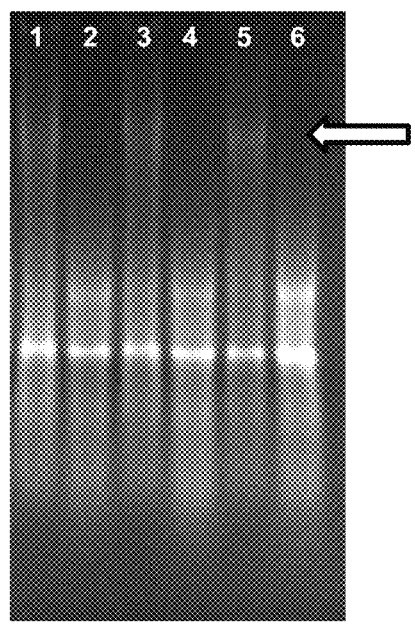

FIG. 7 shows a 1% formaldehyde agarose gel of total RNA preparations with an electrophoresis assisted procedure with delayed elution with and w/o DNaseI digestion (see example 5).

EXAMPLES

Examples that are not covered by the claims are provided for comparative purposes.

Abbreviations

CTA: cellulose triacetate
CA: cellulose acetate
UF: ultrafiltration
RC: regenerated cellulose
PES: polyethersulfone
MOPS: 1×MOPS buffer (20 mM MOPS (N-morpholino) propane sulfonic acid), 50 mM NaCl, 10 mM EDTA, pH 7.0)

Example 1: Collection of Total RNA

RNA can be isolated using an electric field based procedure in a device as shown in the figures. 10 µg of total RNA was spiked into lysis buffer RLT to a total volume of 350 µl. Then, 350 µl of 70% ethanol was added and mixed with 15 µl of magnetic silica particles (Qiagen, MAS G) for 3 min at 1400 rpm. Magnetic particles with bound RNA were transferred to the loading chamber of the flooded device. The housing of said device was provided by a silicon tube (inner/outer diameter: 6/10 mm). A 100 kD (Fa. Sartorius, PES) or a 10 kDa (Fa. Millipore, RC) collection membrane was fixed at the front end by retainer rings. As closing matrix, an agarose-soaked cellulose-Acetate (CA) filter was used.

The electric field based separation was performed for 40 min at 10 V/cm in 50 mM Tris pH 8.5 running buffer. The RNA was collected at the collecting membrane and the purified RNA was withdrawn from the eluate chamber with a pipette (total volume each: 200 µl). The results are shown in FIG. 4. As can be seen from the spike-in experiment, the method allows isolating RNA. However, the used set-up was not optimized for RNA and the pH of the running buffer was too high for RNA. However, the RNA yield must be improved and the RNA needs protection during the purification process to reduce degradation.

Example 2: Electric Field Based RNA Separation

Rat kidney tissue (RNAlater stabilized) was lysed according to the RNeasy protocol with buffer RLT and RTLplus (QIAGEN) and 2×15s homogenization with a TissueRaptor. Aliquots of 400 µl lysate were used for each preparation. 300 µl ethanol was added to 400 µl lysate and 15 µl of magnetic silica particles (MASG, QIAGEN). The binding mixture was incubated for 3 min with 1400 rpm on an Eppendorf Thermomixer to allow binding of the RNA to the beads. The magnetic silica particles with the bound RNA were then transferred with a Pick-Pen into the loading chamber of a cartridge.

Cartridge Design:
Collection matrix: 10 kDa RC membrane (Millipore; Cat.No.: PLGC04710)
Separation matrix: CA-filter
Closing matrix: 10 kDa RC membrane (Millipore; Cat.No.: PLGC04710)

The cartridges were placed in an electrophoresis chamber. 1×MOPS was used as running buffer. The electric field (10 V/cm) was applied for 40 min and reversed for 1 min to simplify the collection of the purified RNA. An RNeasy protocol with RTL and RTLplus lysis buffer was used as a reference.

The eluates were analyzed on a 1% formaldehyde agarose gel. The results showed that the RNA showed degradation in the eluates obtained from the cartridge based purification process. This loss in RNA is presumably due to the re-activation of RNases (in particular originating from the biological sample) after dilution of the chaotropic lysis buffer in the low-salt running buffer.

Example 3: Electric Field Based RNA Separation Using RNase Inhibitors

Rat kidney tissue (RNAlater stabilized) was lysed according to the RNeasy protocol with buffer RTLplus (QIAGEN) and 2×15s homogenization with a TissueRaptor. Aliquots of 400 µl lysate were used for each preparation. 300 µl ethanol was added to 400 µl lysate and 15 µl of magnetic silica particles (MASG, QIAGEN). The binding mixture was incubated for 3 min with 1400 rpm on an Eppendorf Thermomixer to allow binding of the RNA to the beads. The magnetic silica particles with the bound RNA were then transferred to fresh tubes comprising the buffer with or w/o further additives, as indicated in the subsequent table. The magnetic particles were shaked for 3 min at 1400 rpm in a thermomixer to effectively elute the nucleic acids from the beads. The different suspensions comprising the beads and the eluted nucleic acids were then transferred into the prepared cartridges. The loading chambers were correspondingly pre-loaded with MOPS-buffer w/o or with different RNase inhibitors and with or w/o DNase as indicated.

| Set-up | Buffer and additives | Lane in FIG. 5 |
|---|---|---|
| 1 | 200 µl 1× MOPS | 4 |
| 2 | 180 µl 1× MOPS, 10 µl QIAGEN RNase inhibitor, 10 µl NEB RNase inhibitor | 5 |
| 3 | 180 µl 1× MOPS, 10 µl QIAGEN RNase Inhibitor + 10 µl NEB RNase Inhibitor; +10 µl DNase I solution | 6 |
| 4 | 180 µl 1× MOPS, 10 µl QIAGEN RNase Inhibitor + 10 µl NEB RNase Inhibitor; +10 µl DNase I solution | 7 |

Cartridge Design:
Collection matrix: 10 kDa RC membrane (Millipore; Cat.No.: PLGC04710)
Separation matrix: CA-filter
Closing matrix: CTA, glossy side outwards An RNeasy protocol with RTLplus lysis buffer was used as a reference.

The eluates obtained with the RNeasy references and the different cartridge set-ups were analyzed on a 1% formaldehyde agarose gel (lanes 1 to 3, RNeasy reference (5 µl); lanes 4 to 7 (eluates from set-ups 1 to 4 (20 µl)). The results are shown in FIG. 5. The gel shows for the cartridge based approaches RNA degradation in the eluates wherein no RNase inhibitors were used to protect the RNA (lane 4/set-up 1), DNA contamination in the eluates without DNase I (lanes 4 and 5/set-ups 1 and 2) and only slight degradation of the 28S rRNA in the eluates that were obtained with RNase inhibitors (lanes 5, 6, 7/set-ups 2, 3 and 4). Therefore, including an RNase inhibitor can prevent the degradation of RNA during the electric field based purification process. The additional use of DNase can improve the results.

Example 4: Electric Field Based RNA Separation with Delayed Elution According to the Invention Rat kidney tissue (RNAlater stabilized) was lysed according to the RNeasy protocol with buffer RTL (QIAGEN) and 2×15s homogenization with a TissueRaptor. Aliquots of 400 µl lysate were used for each preparation. 300 µl ethanol was added to 400 µl lysate and 15 µl of magnetic silica particles (MASG, QIAGEN). The binding mixture was incubated for 3 min with 1400 rpm on an Eppendorf Thermomixer to allow binding of the RNA to the beads. The loading chambers of 8 cartridges were preloaded with different liquid media and the magnetic silica particles with the bound RNA were then transferred with a Pick-Pen into the loading chamber of a cartridge:
Cartridge Design:
Collection matrix: 10 kDa CTA membrane (Sartorius, Cat-No.: 14539-47-D)
Separation matrix: CA-filter
Closing matrix: glass fiber (GF/B) (cartridges 1 to 4) or 10 kDa CTA (cartridges 5 to 8)
Cartridges 1 and 5: Loading chamber with buffer RPE (QIAGEN; 80% ethanol)
Cartridges 2 and 6: Loading chamber with buffer RPE, 10 µl QIAGEN RNase inhibitor, 10 µl NEB RNase inhibitor
Cartridges 3 and 7: Loading chamber with buffer RPE/water 1:1 (=40% ethanol in the loading chamber)
Cartridges 4 and 8: Loading chamber with buffer RPE/water 1:1 (=40% ethanol in the loading chamber), 10 µl QIAGEN RNase inhibitor, 10 µl NEB RNase inhibitor The cartridges were placed in an electrophoresis chamber. 1×MOPS was used as running buffer. The electric field (10 V/cm) was applied for 40 min and reversed for 20 sec to simplify the collection of the purified RNA. An RNeasy protocol was used as a reference. The eluates obtained with the RNeasy references and the different cartridge set-ups were analyzed on a 1% formaldehyde agarose gel. FIG. 6 shows the results. Lanes 1-6: RNeasy reference in triplicates, two different amounts of eluate Lanes 7-14: RNA isolated using a cartridge based purification approach as described above (cartridges 1 to 8). The result demonstrates that the cartridge based approaches allowed the isolation of RNA with a good 18s/28S rRNA ratio which demonstrates the effectiveness of the new approach despite the simplicity of the procedure. Placing the solid phase with the bound RNA together with a liquid medium comprising a water-miscible organic solvent as taught herein into the loading chamber effectively prevented degradation of the RNA, thereby improving the quality and yield of the isolated RNA. Also apparent is the influence of the cartridge configuration on the RNA yield. Thus, by optimizing the combination of matrixes, the total RNA yield can be further increased.

The comparison of samples with and w/o RNase inhibitors also shows that there is no need for expensive RNase inhibitors to protect the RNA. Instead, it is possible to use a liquid medium which comprises a water-miscible organic solvent such as here 40-80% ethanol. The ethanol comprised in the liquid secures binding of the RNA to the particles when the electric field based separation begins. Thus, the RNA remains initially bound to the particles, while RNases, which are basic proteins with a positive charge, migrate towards the cathode. Upon dilution of the liquid medium in the loading chamber elution of the RNA is initiated. However, the delayed elution approach prevents a substantial contact between active/reactivated RNases and the RNA and hence prevents that the RNA is quickly degraded in the loading chamber. Therefore, the delayed elution approach according to the invention is highly effective in preserving the integrity of the RNA during preparation. The process is simple and does not rely on expensive substances such as RNase inhibitors.

Example 5: Quality Control of Electric Field Based RNA Separation with Delayed Elution Approx. 120 mg rat kidney tissue (RNAlater stabilized) was lysed in 4.8 ml buffer RLTplus with 24 µl Reagent DX according to the RNeasy Plus protocol and 2×15s homogenization with a TissueRaptor. Aliquots of 400 µl lysate (=10 mg tissue) were used for each preparation. 300 µl ethanol was added to 400 µl lysate and 15 µl of magnetic silica particles (MASG, QIAGEN). The binding mixture was incubated for 3 min with 1400 rpm on an Eppendorf Thermomixer to allow binding of the RNA to the beads. The magnetic silica particles with the bound RNA were then transferred with a Pick-Pen into the loading chamber of a cartridge:
Cartridge Design:
Collection matrix: 10 kDa CTA membrane
Separation matrix: CA-filter (cigarette filter)
Closing matrix: glass fiber (GF/B)
The loading chambers were prefilled with
Buffer RPE/water 1:1 (=40% ethanol in the loading chamber)
40% isopropanol in water or
40% DMSO in water.

The cartridges were placed in an electrophoresis chamber. 1×MOPS was used as running buffer. The electric field (10 V/cm) was applied for 40 min and reversed for 20 sec to simplify the collection of the purified RNA. An RNeasy protocol with RTLplus lysis buffer was used as a reference. 3 µl of the eluates (cartridge based purification and RNeasy) were used for analysis on a RNA 6000 Nanochip with an Agilent Bioanalyzer according to the handbook. The electropherograms showed a good 28S/18S peak ratio and good RIN values. The additional use of RNase inhibitors showed no improvement (data not shown) demonstrating a sufficient inhibition of RNA-degrading enzyme by the organic solvents during the delayed elution step.

In an extension of this experiment the preparations with 40% of an organic solvent were also done with DNaseI and Buffer RDD (DNase reaction buffer, QIAGEN) also preloaded into the eluate chamber (10 µl DNase I plus 70 µl RDD). Otherwise, the conditions were the same.

The total RNA eluates obtained with the different cartridge set-ups and delayed elution approaches with and w/o DNase digestion were analysed on a 1% formaldehyde agarose gel. FIG. 7 shows the results. Lane 1: 40% ethanol; Lane 2: 40% ethanol, DNase I; lane 3: 40% isopropanol; lane 4: 40% isopropanol, DNase I; lane 5: 40% DMSO; lane 6: 40% DMSO, DNase I. The arrow indicates DNA contamination in samples w/o DNase I digest. The results demonstrate that the classical DNA removal by including a DNase digestion step in the protocol can also be applied in the cartridge based workflow and that this can further improve the quality of the RNA.

Example 6: Isolation of Small RNA Using a Collection Matrix Having a Low MWCO

The MWCO of the collection matrix influences the size of the recovered target nucleic acid. This is shown here for small RNA. Approx. 110 mg rat kidney tissue (RNAlater stabilized) was lysed in 4.4 ml buffer RLTplus (with beta-mercaptoethanol) with 22 µl Reagent DX according to the RNeasy Plus protocol and 2×15s homogenization with a TissueRaptor. Aliquots of 400 µl lysate (=10 mg tissue) were used for each preparation. Each aliquot was contacted with 20 µl proteinase K and 25 µl of magnetic silica particles (MASG, QIAGEN). 300 µl ethanol was added and the binding mixture was incubated for 3 min with 1400 rpm on an Eppendorf Thermomixer to allow binding of the RNA to the beads. The magnetic silica particles with the bound RNA were then separated using a magnet and the supernatant discarded. The magnetic particles with the bound RNA was contacted with 180 µl MOPS+10 µl DNase I, 10 µl QIAGEN RNase inhibitor, 10 µl RNase inhibitor NEB and shaked for 3 min at 1400 rpm to elute the nucleic acids from the beads. The suspension comprising the magnetic particles and the eluted target nucleic acids was then transferred into the loading chamber of a cartridge:

Cartridge Design:
Collection matrix: Millipore Ultracell UF-membrane (RC), either 10 kDa, 5 kDa, 3 kDa and 1 kDa (each set up was tested in duplicate)
Separation matrix: CA-filter (cigarette filter)
Closing matrix: glass fiber (GF/B)

The cartridges were placed in an electrophoresis chamber. 1×MOPS was used as running buffer. The electric field (10 V/cm) was applied for 40 min (250V) and reversed for 20 sec to simplify the collection of the purified RNA. 100 ml eluate was collected from the collection chamber. The RNA containing eluate was subjected to a miScript Reverse Transcription and miScript PCR. Analysis of the CT values demonstrated that the recovery of small miRNA was improved when using a collection membrane with a lower cut-off value. The lowest Ct values were achieved with the 1 kDa ultrafiltration membrane, the Ct values rose with increasing MWCO. The difference between the 1 kDa collection membrane and the 10 kDa collection membrane was approx. 3Cts. The results are summarized in the subsequent table:

| MWCO collection membrane | Ct miScript PCR with miR25 primer assay |
|---|---|
| 10 kDa | 28.98 |
| 5 kDa | 26.98 |
| 3 kDa | 26.39 |
| 1 kDa | 25.83 |

The invention claimed is:

1. An electrophoresis assisted method for purifying a target nucleic acid from a nucleic acid containing sample, comprising
    (a) binding the target nucleic acid to a solid phase;
    (b) placing the solid phase with the bound target nucleic acid into a loading chamber of a device, wherein the device comprises a passage which comprises the loading chamber and a liquid permeable collection matrix and wherein the solid phase with the bound target nucleic acid is present in the loading chamber in a liquid medium comprising at least one water-miscible organic solvent and wherein the target nucleic acid remains bound to the solid phase in said liquid medium;
    (c) generating an electric field between a cathode and an anode and using a running solution that conducts the electric current, wherein the running solution dilutes the liquid medium comprised in the loading chamber resulting in elution of the bound target nucleic acid, and wherein the eluted target nucleic acid migrates according to its charge in the electric field and is retained by the collection matrix;
    (d) collecting the purified target nucleic acid.

2. The method according to claim 1, wherein the target nucleic acid is RNA.

3. The method according to claim 1, wherein the water-miscible organic solvent has one or more of the following characteristics
    a) it is selected from aprotic polar solvents and protic solvents;
    b) it is selected from aliphatic, short chained branched or unbranched alcohols with optionally one to five carbon atoms, optionally selected from methanol, ethanol, propanol, isopropanol and butanol, optionally selected from ethanol and isopropanol; and/or
    c) it is selected from sulfoxides, ketones, nitriles, cyclic or aliphatic ethers, lactams and tertiary carboxylic acid amides and is optionally selected from the group consisting of acetone, acetonitrile, dimethyl sulfoxide (DMSO), tetra hydrofuran (THF), dioxane and dimethylformamide (DMF).

4. The method according to claim 1, wherein the liquid medium comprises the at least one water-miscible organic solvent in a concentration from 25% to 95% (v/v).

5. The method according to claim 1, having one or more of the following characteristics:
    a) the liquid medium is present in the loading chamber before the solid phase with the bound target nucleic acid is added; and/or
    b) the solid phase with the bound target nucleic acid is contacted with the liquid medium, and the liquid medium comprising the solid phase with the bound target nucleic acid is placed into the loading chamber;
    c) the liquid medium is an aqueous medium which optionally comprises a salt and/or buffering agent; and/or
    d) the liquid medium comprises a DNase.

6. The method according to claim 1, wherein the running solution has one or more of the following characteristics:
    i) it is suitable to effect elution of the target nucleic acid from the solid phase;
    ii) it has a pH that lies in the range of 5 to 9;
    iii) it comprises a buffering agent which has a buffering capacity that lies within the range of pH 6 to 8, wherein optionally, the buffering agent is MOPS or Tris;
    iv) it comprises a buffering agent in a concentration from 7.5 mM to 100 mM;
    v) it comprises at least one salt, optionally an alkali metal salt; and/or
    vi) it is compatible with a subsequent nucleic acid analysis method.

7. The method according to claim 1, wherein the solid phase has one or more of the following characteristics
    a) the solid phase is provided by particles, optionally silica or glass particles;
    b) the solid phase is provided by magnetic particles;
    c) the solid phase provides a silicon containing surface; and/or d) the solid phase provides a siliceous surface, optionally an unmodified siliceous surface.

8. The method according to claim 1, wherein step (a) comprises optionally lysing the sample and binding the target nucleic acid to the solid phase in the presence of a salt, wherein binding is optionally assisted by at least one water-miscible organic solvent.

9. The method according to claim 1, wherein the device comprises a passage which comprises the loading chamber, a liquid permeable separation matrix adjacent to the loading chamber and a liquid permeable collection matrix.

10. The method according to claim 1, for isolating RNA as target nucleic acid from a biological sample, comprising
   (a) lysing the biological sample in the presence of at least one chaotropic salt and binding RNA to particles providing a silicon containing surface, wherein binding occurs in the presence of the at least one chaotropic salt and optionally at least one water-miscible organic solvent,
   (a) placing the solid phase with the bound RNA into a loading chamber of a device, wherein the device comprises a passage which comprises the loading chamber at one end, a liquid permeable separation matrix adjacent to the loading chamber and a liquid permeable collection matrix at the other end and wherein the solid phase with the bound RNA is present in the loading chamber in an aqueous liquid medium comprising at least one water-miscible organic solvent in a concentration that lies in the range of 30% to 90% (v/v) and wherein the RNA remains bound to the solid phase in said aqueous medium;
   (b) generating an electric field between a cathode and an anode and using a running solution that conducts the electric current, wherein the running solution dilutes the aqueous liquid medium in the loading chamber resulting in elution of the bound RNA upon dilution of the aqueous liquid medium, and wherein the eluted RNA migrates according to its charge in the electric field through the separation matrix and is retained by the collection matrix;
   (c) optionally reversing the electric field and collecting the purified RNA.

11. The method according to claim 1, wherein the device has an elongated body, optionally tube-shaped, which comprises in the passage the loading chamber that is formed at least in part by a liquid permeable closing matrix and the separation matrix and wherein the solid phase with the bound target nucleic acid is placed into the loading chamber, optionally through an opening; and wherein the device comprises in the passage a collection chamber that is formed at least in part by the separation matrix and a liquid permeable collection matrix and wherein the eluted target nucleic acid is collected from the collection chamber, optionally through an opening.

12. The method according to claim 1, wherein the liquid medium comprises the at least one water-miscible organic solvent in a concentration from 30% to 90% (v/v).

13. The method according to claim 1, wherein the liquid medium comprises the at least one water-miscible organic solvent in a concentration from 35% to 85% (v/v).

14. The method according to claim 1, wherein the running solution has one or more of the following characteristics:
   i) it is suitable to effect elution of the target nucleic acid from the solid phase;
   ii) it has a pH that lies in the range of 6.5 to 7.5;
   iii) it comprises a buffering agent which has a buffering capacity that lies within the range of pH 6 to 8, wherein optionally, the buffering agent is MOPS or Tris;
   iv) it comprises a buffering agent in a concentration from 17.5 mM to 30 mM;
   v) it comprises at least one salt, optionally an alkali metal salt; and/or
   vi) it is compatible with a subsequent nucleic acid analysis method.

15. A kit for use in a electrophoresis assisted method for purifying a target nucleic acid from a nucleic acid containing sample, comprising
   (a) a device comprising a passage which comprises a loading chamber and a liquid permeable collection matrix; and
   (b) a liquid medium comprising at least one water-miscible organic solvent in a concentration in a range of 25% to 95% (v/v);
   (c) optionally a running solution;
   (d) optionally a solid phase for binding the target nucleic acid;
   (e) optionally a lysis reagent and/or a binding reagent.

16. The kit according to claim 15, wherein said passage further comprises, a liquid permeable separation matrix adjacent to the loading chamber.

17. Kit according to claim 15, having one or more of the following characteristics:
   a) the device has an elongated body, optionally tube-shaped, which comprises in the passage the loading chamber that is formed at least in part by a liquid permeable closing matrix and a separation matrix and wherein the solid phase with a bound target nucleic acid is placed into the loading chamber, optionally through an opening; and wherein the device comprises in the passage a collection chamber that is formed at least in part by the separation matrix and a liquid permeable collection matrix and wherein an eluted target nucleic acid is collected from the collection chamber, optionally through an opening;
   b) the liquid medium has one or more of the characteristics
      b1) it is selected from aprotic polar solvents and protic solvents;
      b2) it is selected from aliphatic, short chained branched or unbranched alcohols with optionally one to five carbon atoms, optionally selected from methanol, ethanol, propanol, isopropanol and butanol, optionally selected from ethanol and isopropanol; and/or
      b3) it is selected from sulfoxides, ketones, nitriles, cyclic or aliphatic ethers, lactams and tertiary carboxylic acid amides and is optionally selected from the group consisting of acetone, acetonitrile, dimethyl sulfoxide (DMSO), tetrahydrofuran (THF), dioxane and dimethylformamide (DMF);
   c) the optional running solution has one or more of the characteristics
      c1) it is suitable to effect elution of the target nucleic acid from the optional solid phase;
      c2) it has a pH that lies in the range of 5 to 9;
      c3) it comprises a buffering agent which has a buffering capacity that lies within the range of pH 6 to 8, wherein optionally, the buffering agent is MOPS or Tris;
      c4) it comprises a buffering agent in a concentration selected from 7.5 mM to 100 mM;
      c5) it comprises at least one salt, optionally an alkali metal salt; and/or c6) it is compatible with a subsequent nucleic acid analysis method;
d) the optional solid phase has one or more of the characteristics
   d1) the optional solid phase is provided by particles, optionally silica or glass particles;
   d2) the optional solid phase is provided by magnetic particles;
   d3) the optional solid phase provides a silicon containing surface; and/or
   d4) the optional solid phase provides a siliceous surface, optionally an unmodified siliceous surface; and/or
e) the optional lysis reagent and/or the binding reagent comprises a salt, optionally a chaotropic salt.

18. Kit according to claim 15, having one or more of the following characteristics:
a) the device has an elongated body, optionally tube-shaped, which comprises in the passage the loading chamber that is formed at least in part by a liquid permeable closing matrix and a separation matrix and wherein the solid phase with a bound target nucleic acid is placed into the loading chamber, optionally through an opening; and wherein the device comprises in the passage a collection chamber that is formed at least in part by the separation matrix and a liquid permeable collection matrix and wherein an eluted target nucleic acid is collected from the collection chamber, optionally through an opening;
b) the liquid medium has one or more of the characteristics
   b1) it is selected from aprotic polar solvents and protic solvents;
   b2) it is selected from aliphatic, short chained branched or unbranched alcohols with optionally one to five carbon atoms, optionally selected from methanol, ethanol, propanol, isopropanol and butanol, optionally selected from ethanol and isopropanol; and/or
   b3) it is selected from sulfoxides, ketones, nitriles, cyclic or aliphatic ethers, lactams and tertiary carboxylic acid amides and is optionally selected from the group consisting of acetone, acetonitrile, dimethyl sulfoxide (DMSO), tetrahydrofuran (THF), dioxane and dimethylformamide (DMF);
c) the optional running solution has one or more of the characteristics
   c1) it is suitable to effect elution of the target nucleic acid from the optional solid phase;
   c2) it has a pH that lies in the range of 6.5 to 7.5;
   c3) it comprises a buffering agent which has a buffering capacity that lies within the range of pH 6 to 8, wherein optionally, the buffering agent is MOPS or Tris;
   c4) it comprises a buffering agent in a concentration selected from 17.5 mM to 30 mM;
   c5) it comprises at least one salt, optionally an alkali metal salt; and/or
   c6) it is compatible with a subsequent nucleic acid analysis method;
d) the optional solid phase has one or more of the characteristics
   d1) the optional solid phase is provided by particles, optionally silica or glass particles;
   d2) the optional solid phase is provided by magnetic particles;
   d3) the optional solid phase provides a silicon containing surface; and/or
   d4) the optional solid phase provides a siliceous surface, optionally an unmodified siliceous surface; and/or
e) the optional lysis reagent and/or the binding reagent comprises a salt, optionally a chaotropic salt.

* * * * *